(12) United States Patent
Astarci et al.

(10) Patent No.: US 10,292,818 B2
(45) Date of Patent: May 21, 2019

(54) DEVICE FOR EXCISION OF HEART VALVE

(71) Applicants: Universite Catholique De Louvain, Louvain-la-Neuve (BE); Cliniques Universitaires Saint Luc, Woluwe-Saint-Lambert (BE)

(72) Inventors: Parla Astarci, Kraainem (BE); Khanh Tran Duy, Wahlain (BE); Benoît Raucent, Wavre (BE); Xavier Bollen, Marchovelette (BE); Benoît Herman, Brussels (BE)

(73) Assignees: UNIVERSITE CATHOLIQUE DE LOUVAIN, Louvain-la-Neuve (BE); CLINIQUES UNIVERSITAIRES SAINT LUC, Woluwe-Saint-Lambert (BE)

( * ) Notice: Subject to any disclaimer, the term of this patent is extended or adjusted under 35 U.S.C. 154(b) by 760 days.

(21) Appl. No.: 14/385,023

(22) PCT Filed: Mar. 14, 2013

(86) PCT No.: PCT/EP2013/055192
§ 371 (c)(1),
(2) Date: Sep. 12, 2014

(87) PCT Pub. No.: WO2013/135792
PCT Pub. Date: Sep. 19, 2013

(65) Prior Publication Data
US 2015/0088246 A1 Mar. 26, 2015

(30) Foreign Application Priority Data
Mar. 14, 2012 (EP) .................................... 12159531

(51) Int. Cl.
| A61F 2/24 | (2006.01) |
| A61B 17/00 | (2006.01) |
| A61B 17/22 | (2006.01) |
| A61B 17/32 | (2006.01) |

(Continued)

(52) U.S. Cl.
CPC ........ *A61F 2/2427* (2013.01); *A61B 17/3205* (2013.01); *A61B 17/320725* (2013.01);
(Continued)

(58) Field of Classification Search
CPC ........... A61F 2/2427; A61B 17/320725; A61B 17/3205; A61B 17/32053;
(Continued)

(56) References Cited

U.S. PATENT DOCUMENTS

| 6,830,584 B1 | 12/2004 | Seguin |
| 2004/0225355 A1 | 11/2004 | Stevens |

(Continued)

FOREIGN PATENT DOCUMENTS

WO WO-2004/019811 A2 3/2004

OTHER PUBLICATIONS

International Search Report for International Patent Application No. PCT/EP2013/055192, search completed on Jul. 23, 2013, dated Jul. 31, 2013 (5 pages).
International Preliminary Report on Patentability for International Patent Application No. PCT/EP2013/055192, dated Sep. 25, 2014 (13 pages).

*Primary Examiner* — Katrina M Stransky
*Assistant Examiner* — Michael G Mendoza
(74) *Attorney, Agent, or Firm* — Clark & Elbing LLP; Susan M. Michaud

(57) ABSTRACT

A device (100) for the excision of a heart valve via a percutaneous route having a proximal (20) and distal (30) end, comprising an expandable cutting instrument, ECI, that forms a receptacle in the open configuration for receiving, compacting and containing the excised heart valve, an expandable cutting block, ECB, and a displacement mechanism (5, 6) for adjusting the distance between the ECI and the ECB (70).

14 Claims, 12 Drawing Sheets

(51) Int. Cl.
  *A61B 17/3205* (2006.01)
  *A61B 17/3207* (2006.01)

(52) U.S. Cl.
  CPC . *A61B 17/32053* (2013.01); *A61B 17/320758* (2013.01); *A61B 2017/00783* (2013.01); *A61B 2017/22061* (2013.01); *A61B 2017/320052* (2013.01); *A61B 2017/320064* (2013.01); *A61B 2017/320716* (2013.01)

(58) Field of Classification Search
  CPC .. A61B 17/320758; A61B 2017/00783; A61B 2017/320716; A61B 2017/22061; A61B 2017/320064; A61B 2017/320052
  See application file for complete search history.

(56) References Cited

U.S. PATENT DOCUMENTS

| | | | |
|---|---|---|---|
| 2005/0187616 A1* | 8/2005 | Realyvasquez | A61F 2/2427 623/2.11 |
| 2005/0203549 A1* | 9/2005 | Realyvasquez | A61B 17/11 606/142 |
| 2005/0209674 A1* | 9/2005 | Kutscher | A61B 17/22 623/1.11 |
| 2006/0074484 A1 | 4/2006 | Huber | |
| 2010/0268226 A1* | 10/2010 | Epp | A61B 18/1492 606/48 |

* cited by examiner

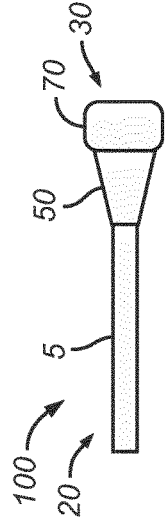
Fig. 14
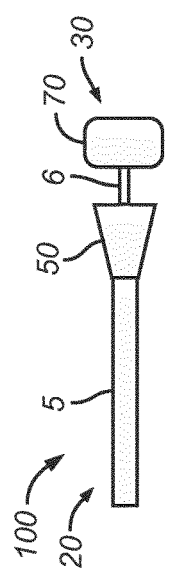
Fig. 15
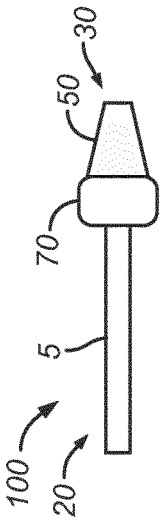
Fig. 16
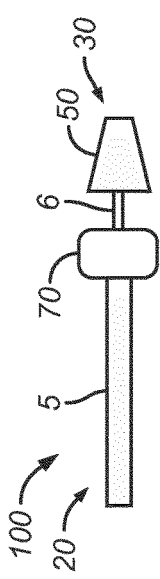
Fig. 17
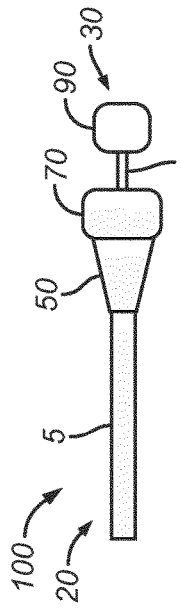
Fig. 18
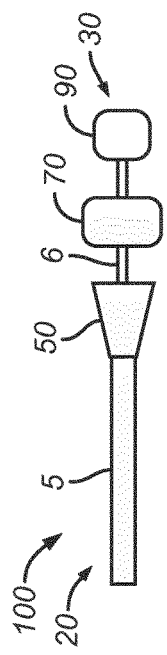
Fig. 19
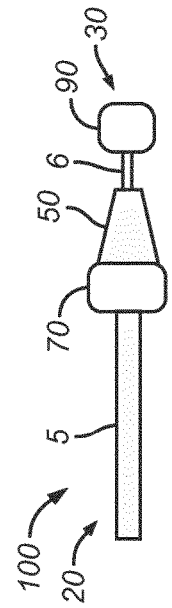
Fig. 20
Fig. 21

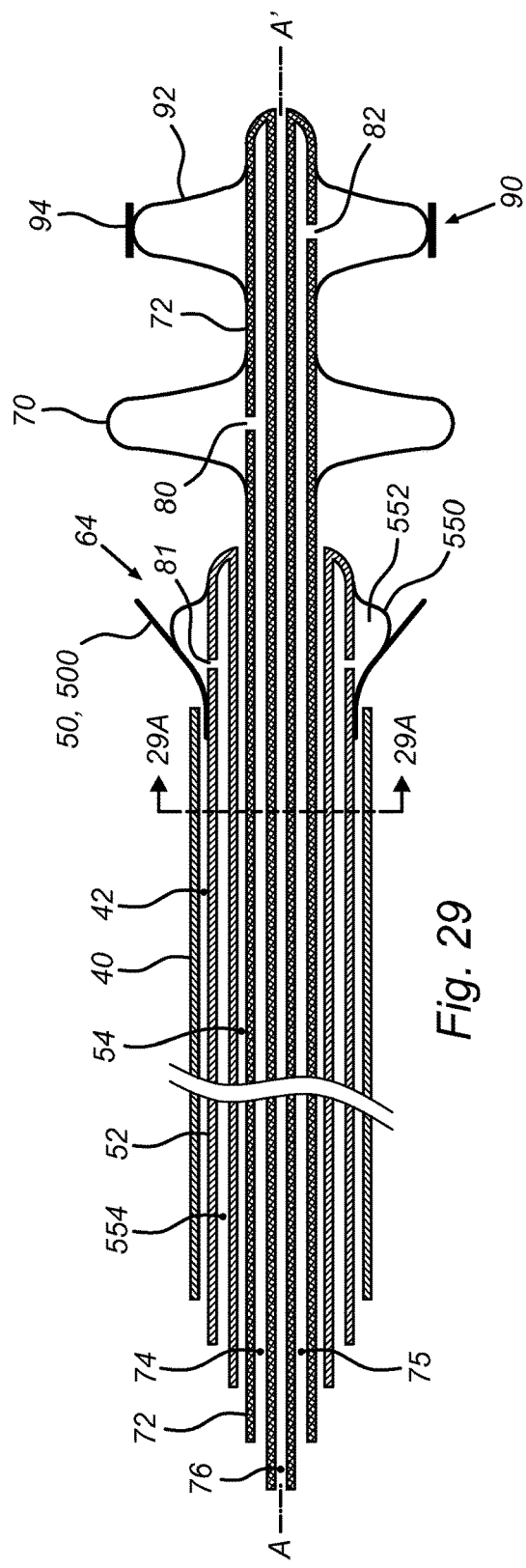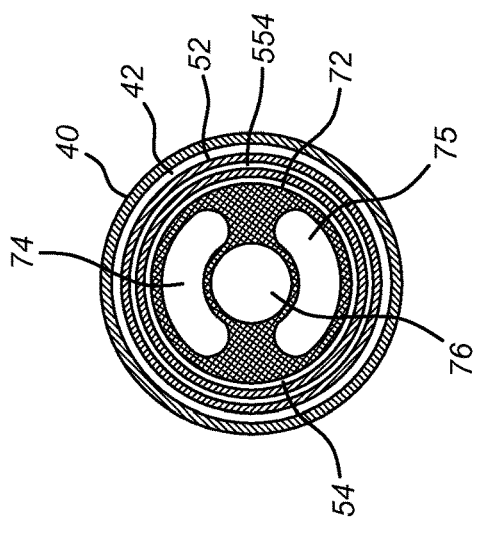

DEVICE FOR EXCISION OF HEART VALVE

FIELD OF THE INVENTION

The present invention is in the field of a device for performing excision of a heart valve, by a minimally invasive procedure. It further relates to an integrated device for performing endovascular excision of a heart valve, and deployment and positioning of a new percutaneous heart valve.

BACKGROUND OF THE INVENTION

Essential to normal heart function are four heart valves, which allow blood to pass through the four chambers of the heart in one direction. The valves have either two or three cusps, flaps, or leaflets, which comprise fibrous tissue that attaches to the walls of the heart. The cusps open when the blood flow is flowing correctly and then close to form a tight seal to prevent backflow.

The four chambers are known as the right and left atria (upper chambers) and right and left ventricles (lower chambers). The four valves that control blood flow are known as the tricuspid, mitral, pulmonary, and aortic valves. In a normally functioning heart, the tricuspid valve allows one-way flow of deoxygenated blood from the right upper chamber (right atrium) to the right lower chamber (right ventricle). When the right ventricle contracts, the pulmonary valve allows one-way blood flow from the right ventricle to the pulmonary artery, which carries the deoxygenated blood to the lungs. The mitral valve, also a one-way valve, allows oxygenated blood, which has returned to the left upper chamber (left atrium), to flow to the left lower chamber (left ventricle). When the left ventricle contracts, the oxygenated blood is pumped through the aortic valve to the aorta.

Certain heart abnormalities result from heart valve defects, such as valvular insufficiency. Valve insufficiency is a common cardiac abnormality where the valve leaflets do not completely close. This allows regurgitation (i.e., backward leakage of blood at a heart valve). Such regurgitation requires the heart to work harder as it must pump both the regular volume of blood and the blood that has regurgitated. Obviously, if this insufficiency is not corrected, the added workload can eventually result in heart failure.

Another valve defect or disease, which typically occurs in the aortic valve is stenosis or calcification. This involves calcium buildup in the valve which impedes proper valve leaflet movement. Treatment typically involves removal of the leaflets and replacement with valve prosthesis during conventional open surgery. In minimal invasive surgery, the prosthesis is currently implanted without resection of the native valve. Hence it can produce an inhomogeneous and non-circular calcific layer, leading to distortion and geometry change of the prosthesis and of the aortic annulus, respectively. Paravalvular leakage (PVL) and high percentage of total heart block, coronary ostia and even prosthesis-patient mismatch are of concern with a potential negative influence on longterm survival of the patient and on the durability of the implanted prosthesis. Therefore, the endovascular resection of the degenerated native heart valve would be advantageous prior to a catheter-based implantation.

The defective heart valve is typically calcified; removal of the calcified valve requires an instrument that can deliver the appropriate cutting force, at the right place and security margin/reliability. Additionally, the tissue of a diseased heart valve cannot be readily compressed or compacted for withdrawal from the site of intervention through a catheter owing to calcification. Moreover, particular debris formed by the valve needs to be contained.

US 2006/0074484 describes a system for excising a heart valve, comprising a pair of inflatable cutting devices, but the problem of removing the bulky valve through the delivery catheter is not addressed.

There is a need in the art for a device which can perform removal efficiently and accurately, and optionally position and deploy a replacement valve in a single device.

LEGENDS TO THE FIGURES

FIGS. 7-10 are a view of an ECI that is an expandable cone, attached to a displacement mechanism ($1^{st}$ elongate member), indicating stepwise withdrawal of the expandable cone a delivery catheter.

FIG. 14 shows a device of the invention having an arrangement of an ECI and ECB together with a displacement means (longitudinal members) wherein the cutting edge of the ECI points in a distal direction, and the ECI and ECB are spatially separated.

FIG. 15 shows a device of the invention having arrangement of FIG. 14, where the ECI and ECB are in mutual contact, and forming a closed receptacle.

FIG. 16 shows a device of the invention having an arrangement of an ECI and ECB together with a displacement means (longitudinal members) wherein the cutting edge of the ECI points in a proximal direction, and the ECI and ECB are spatially separated.

FIG. 17 shows a device of the invention having an arrangement of FIG. 16, where the ECI and ECB are in mutual contact, and forming a closed receptacle.

FIG. 18 shows a device of the invention having an arrangement of an ECI, ECB, and IDU together with a displacement means (longitudinal members) wherein the cutting edge of the ECI points in a distal direction, and the ECI and ECB are spatially separated.

FIG. 19 shows a device of the invention having an arrangement of FIG. 18, where the ECI and ECB are in mutual contact, and forming a closed receptacle.

FIG. 20 shows a device of the invention having an arrangement of an ECI, ECB, and IDU together with a displacement means (longitudinal members) wherein the cutting edge of the ECI points in a proximal direction, and the ECI and ECB are spatially separated.

FIG. 21 shows a device of the invention having an arrangement of FIG. 20, where the ECI and ECB are in mutual contact, and forming a closed receptacle.

FIG. 29 depicts a longitudinal cross section of a device of the invention comprising an ECI, ECB, IDU and displacement mechanism, where the ECI and ECB are in an open configuration. The ECI comprises an expandable balloon. A longitudinal axis A-A is indicated.

FIG. 29A depicts a transverse cross section of a device depicted in FIG. 29 along a plane indicated by the line in FIG. 29.

Figure 30:
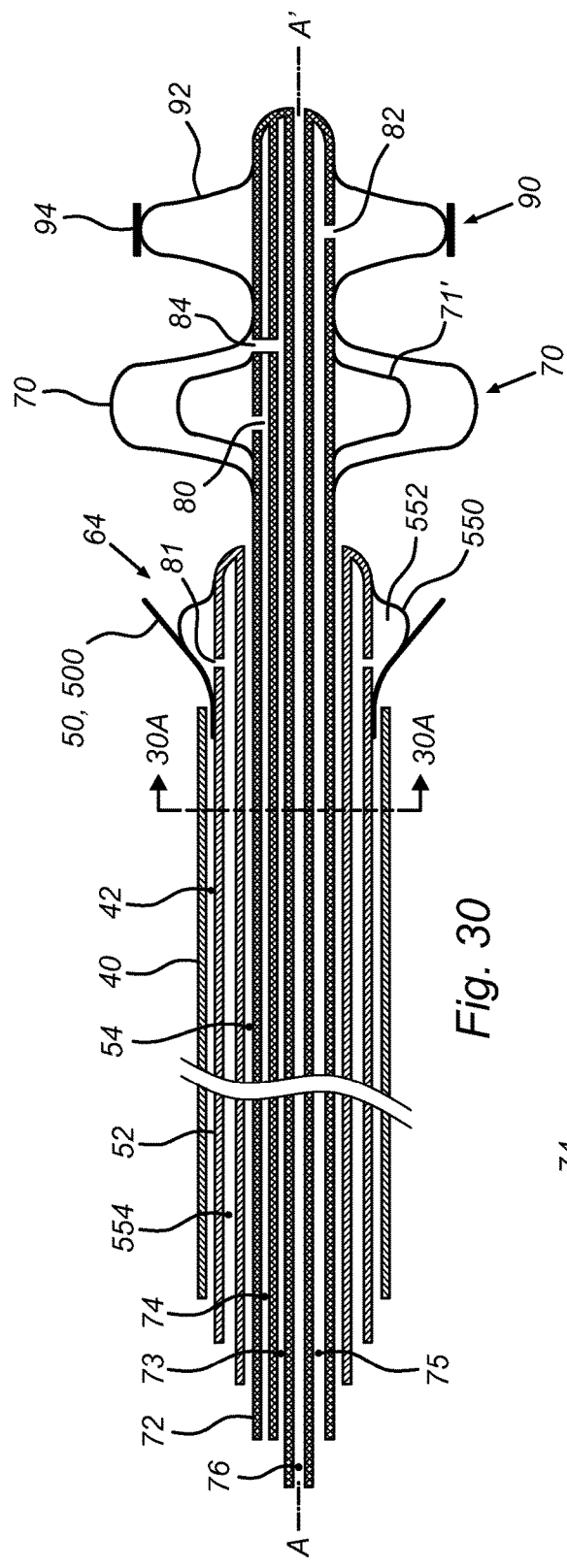

FIG. 30 depicts a longitudinal cross section of a device of the invention comprising an ECI, ECB, IDU and displacement mechanism, where the ECI and ECB are in an open configuration. The ECI comprises an expandable balloon, and the ECB comprises a double balloon. A longitudinal axis A-A is indicated.

Figure 30A:
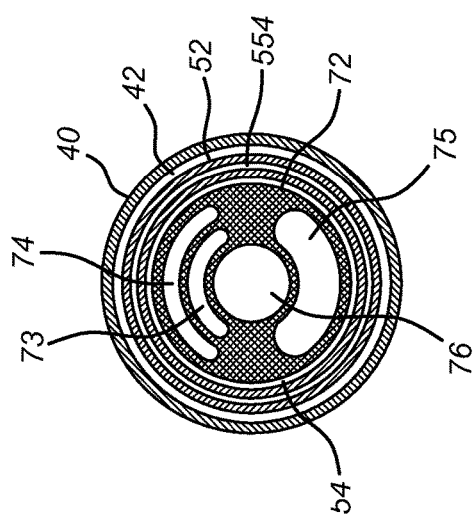

FIG. 30A depicts a transverse cross section of a device depicted in FIG. 30 along a plane indicated by the line in FIG. 30.

Figure 31:
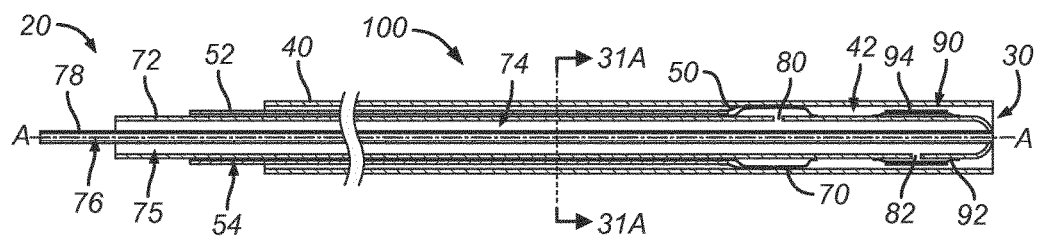

FIG. 31 depicts a longitudinal cross section of a device of the invention comprising an ECI, ECB, IDU and displacement mechanism, where the ECI and ECB are in a closed configuration. A longitudinal axis A-A is indicated.

Figure 31A:
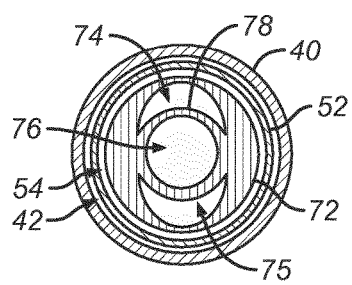
Figure 32:
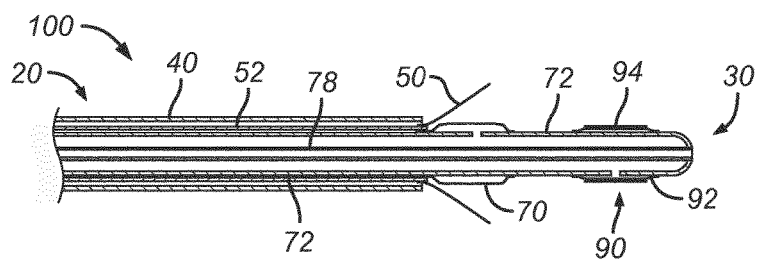
Figure 33:
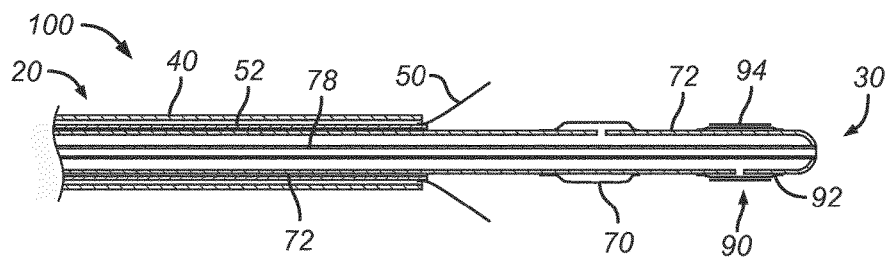
Figure 34:
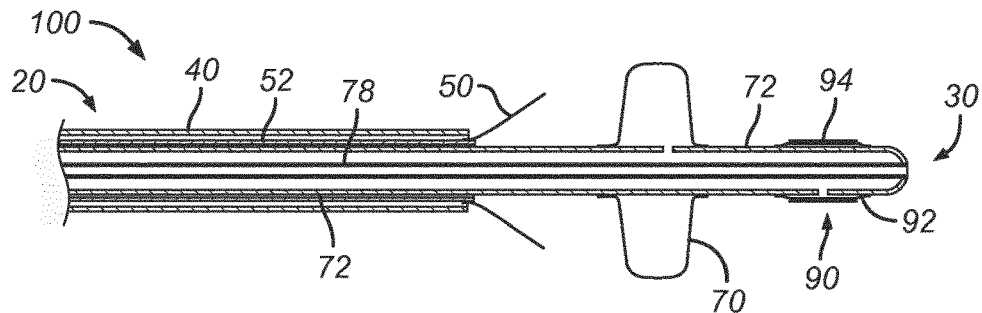

FIG. 31A depicts a transverse cross section of a device depicted in FIG. 31 along a plane indicated by the line in FIG. 31.

FIGS. 32 to 40 depict steps in the use of a device indicated in FIG. 31 for excising a heart valve, and deployment of a replacement (prosthetic) heart valve.

Figure 41A:

FIGS. 41A and B depict an excised heart valve (A) in the native (uncompressed or uncompacted or unfolded) state, and its compaction or compression or folding (B) into a cylindrical form.

SUMMARY OF SOME EMBODIMENTS THE INVENTION

One embodiment of the invention is a device (100) for the excision of a heart valve via a percutaneous route having a proximal (20) and distal (30) end, comprising:
a radially expandable cutting instrument, ECI, (50, 50') capable of radial expansion from a closed (50') to an open (50) configuration,
  wherein the open configuration provides a receptacle with a void (64) having an aperture (65) at one end, the distal edge of the aperture (65) forming a cutting edge (66) for excision of the heart valve,
  which receptacle is configured to receive and contain the excised heart valve,
  wherein the ECI (50') in the closed configuration, is configured for passage through the lumen (42) of a delivery catheter (40),
  wherein the receptacle is configured to compress or compact or fold, and/or store the excised heart valve by contraction of the ECI from the open (50) to the closed configuration (50');
an expandable cutting block, ECB, capable of expansion from a closed (70') to an open (70) configuration, disposed adjacent to the cutting edge (66),
  wherein the ECB in the open configuration (70) provides a support surface (77) to support the heart valve under excision by the ECI (50),
  wherein the ECB in the closed configuration (70'), is configured for passage through the lumen (42) of the delivery catheter (40); and
a displacement mechanism (5, 6) for adjusting the distance between the cutting edge (66) and the ECB (70).

The displacement mechanism may comprise a first elongate member (52) and a second elongate member (72), wherein the ECI (50) is attached to a distal end (30) of the first elongate member (52) and the ECB (70) is attached to a distal end (30) of the second elongate member (72), which first and second members are slidable relative to each other.

The first elongate member (52) may be provided with a lumen (54) extending between the proximal end (20) and the distal end (30) and is open at both ends, configured for the passage of the second elongate member (72).

The second elongate member (72) may be provided with a guidewire lumen extending between the proximal end (20) and the distal end (30) and is open at both ends, configured for the passage of a guidewire.

The ECB (70) may comprise an expandable balloon, and the second elongate member (72) is provided with an inflation lumen in fluidic connection with an inflation lumen of said expandable balloon.

The ECB (72) may comprise two expandable balloons, an outer expandable balloon (71) and an inner expandable balloon (71') provided within a lumen of the outer expandable balloon (71), and the second elongate member (72) is provided with an inner-balloon inflation lumen (74) in fluidic connection with an inflation lumen of said inner-expandable balloon, and with an outer-balloon inflation lumen (73) in fluidic connection with an inflation lumen of said outer-expandable balloon.

The cutting edge (66) may point in a distal (30) direction and concomitantly the support surface (77) points in a proximal (20) direction.

The ECI (50) may be at least partly conical in the expanded (open) configuration.

The ECI (50) may be formed from a series of elongate blades arranged around a ring, each elongate blade pivoted at one end and provided with a cutting edge at the other end, which in the open configuration forms a truncated conical shape.

The ECI may comprise an expandable cone (500) having a sheet of material comprising a geometric shape of an annulus segment. The ECI may comprise an expandable cone formed from a sheet of material comprising a geometric shape of an annulus segment. The expandable cone may be configured to transition from the open to closed configuration by rolling the annulus segment into essentially a cylindrical shape. The rolling may be actuated by the rotation and proximal displacement of the first elongate member (52) relative to the delivery catheter (40).

The ECI (50) and ECB (70) may, in mutual contact, form a closed receptacle formed by the support surface (77) of the ECB co-operating with the receptacle aperture (66).

The device (100) may further comprising an implant deployment unit, IDU (90), comprising a replacement heart valve, which IDU (90) configured to deploy the replacement heart valve upon actuation.

The IDU (90) may be operatively attached to the second elongate member (72), distal (30) to the ECB (70).

The IDU (90) may comprise an expandable balloon around which the replacement heart valve is disposed, and the replacement heart valve is balloon deployable.

The distance between the IDU (90) and the ECB (70) may be fixed.

DETAILED DESCRIPTION OF INVENTION

Before the present method used in the invention is described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal", "distal end", "proximal" and "proximal end" are used through the specification, and are terms generally understood in the field to mean towards (proximal) or away (distal) from the surgeon side of the apparatus. Thus, "proximal (end)" means towards the surgeon side and, therefore, away from the patient side. Conversely, "distal (end)" means towards the patient side and, therefore, away from the surgeon side. In the drawings, the proximal part of an element is indicated with reference sign 20 and the distal part of an element is indicated with reference 30.

The present invention concerns a device for excision of a heart valve via a percutaneous route. The heart valve may be any, for instance, a native diseased valve or a prosthetic valve. The device comprises a radially expandable cutting instrument (ECI) capable of radial expansion from a closed to an open configuration. The ECI is also capable of contraction from an open state to a closed configuration. The ECI in the open state provides a walled receptacle having an aperture at one end. The edge of the aperture forms a cutting edge for excision. The receptacle is configured to receive and contain (store) the excised heart valve. The wall of the receptacle may also prevent or reduce leakage of debris from the excised heart valve. The ECI in the closed configuration, is configured for passage through the lumen of a delivery catheter. The receptacle may be configured to compress or compact or fold the excised heart valve by contraction of the cutting instrument from the open to the closed state. The contraction is typically radial. Compression or compaction or folding forces may be transmitted to the receptacle by its withdrawal into the lumen of the delivery catheter. It will be appreciated that other mechanisms for compression or compaction are envisaged by the present invention.

The device also comprises an expandable cutting block (ECB), capable of expansion from a closed configuration to an open configuration. The ECB is also capable of contraction from an open configuration to a closed configuration. The ECB is disposed adjacent to the cutting edge of the ECI. The ECB in the open state provides a support surface to support the heart valve under excision by the ECI. The ECB in the closed configuration, is configured for passage through the lumen of the delivery catheter. The ECI and ECB are arranged adjacent to each other. Preferably, the central axes of the ECI and ECB are co-axial.

The device also comprises a displacement mechanism for adjusting the distance between the cutting edge and the ECB. Preferably, the displacement mechanism is operatively linked to the compression or compaction function by the ECI i.e. the ECI may compress or compact responsive to movements by the displacement mechanism.

The invention therefore provides a receptacle in the ECI which can hold the excised valve, compress or compact it, and withdraw it. It may be withdrawn through the same narrow delivery catheter used to deploy the ECI and ECB. Thus, for the first time, an excised heart valve can be safely withdrawn through a delivery catheter, thereby reducing the risks of introducing debris from the valve into the vasculature. Such debris may not only be tissue but may include particulate calcium deposits. The invention also accurately excises the heart valve, by virtue of the ECB which can also act to center, and optionally align the cutting blade. Accuracy may further be enhanced using radio-opaque markers provided on the ECI and ECB.

Figure 1:
FIG. 1 is a schematic view of an expandable cutting instrument (ECI) in a closed configuration.
Figure 4:
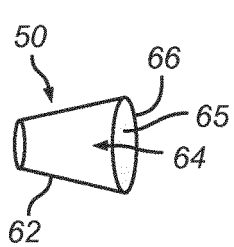
FIG. 4 is a schematic view of an ECI in an open configuration.

With reference to FIGS. 1 and 4, the ECI has a closed 50' and open 50 configuration. In the closed 50' configuration, the ECI has a narrower profile compared with the ECI in the open 50 configuration. In the closed 50' configuration, the ECI is able to pass substantially unhindered through the lumen of a delivery catheter. The ECI is capable of expanding from a closed 50' configuration to an open 50 configuration; this is typical for deployment of the ECI through a delivery catheter where the ECI remains closed while the delivery catheter is advanced, and expands during deployment. The ECI is also capable of contracting from an open 50 configuration to a closed 50' configuration; this is typical when ECI is withdrawn back into the delivery catheter.

Preferably in the closed 50' configuration the ECI has a maximum outer transverse-cross-sectional diameter of 0.5 cm, 0.6 cm, 0.7 cm, 0.8 cm, 0.9 cm, 1 cm, 1.1 cm, 1.2 cm, 1.3 cm, 1.4 cm, 1.5 cm or a value in the range between any two of the aforementioned values, preferably between 0.8 cm to 1.1 cm, most preferably about 0.9 cm Preferably in the open configuration the ECI has a maximum outer transverse-cross-sectional diameter of 1.5 cm, 1.6 cm, 1.7 cm, 1.8 cm, 1.9 cm, 2 cm, 2.1 cm, 2.2 cm, 2.3 cm, 2.4 cm, 2.5 cm, 2.6 cm, 2.7 cm, 2.8 cm or a value in the range between any two of the aforementioned values, preferably between 2 cm to 2.5 cm, most preferably about 2.2 cm.

According to one aspect of the invention, outer transverse-cross-sectional diameter of the ECI 50, 50' in the open configuration is fixed. Alternatively, outer transverse-cross-sectional diameter of the ECI 50, 50' in the open configuration is variable or settable; when it is variable, it may be set at a particular size by the operator, and remain at that size during the procedure.

The ECI 50, 50' may be radially expandable. The ECI may be non-radially expandable. The ECI 50, 50' may be longitudinally expandable. The ECI may be non-longitudinally expandable. Preferably, the ECI 50, 50' is radially expandable and non-longitudinally expandable. The size of the ECI 50, 50' in the open configuration may be adjustable. The ECI 50, 50' may be self-expanding from the closed configuration to the open configuration; in other words, when it is sheathed using a constricting over sheath, the ECI is in a closed configuration. When the ECI is unsheathed, the ECI expands to the open configuration. Such a sheath may be the deliver catheter or a lasso.

It is also within the scope of the invention that the ECI is manually expandable and contractible by the application of force for instance, using a balloon.

Expansion and/or contraction of the ECI 50, 50' may be actuated by an expansion actuation mechanism. Such mechanism which may utilize sheathing/unsheathing, an expandable balloon, or the like. It will be appreciated that the expansion is reversible i.e. the ECI 50, 50' is capable of expansion and contraction. Where the expansion mechanism is an expandable balloon, it is preferably disposed within the receptacle formed by a conical ECI 50, 50'.

A receptacle is formed by the ECI 50 in the open configuration. In other words, the ECI 50 is hollow, the hollow forming a void 64 of the receptacle. The receptacle contains at one end an aperture 65, giving the environment in which the ECI is placed open access to the void 64. At the other end, the receptacle is preferably closed from open access to the environment (retaining end). At the retaining end, the receptacle is preferably attached to a displacement mechanism. In particular, the retaining end is configured such that the excised heart valve, and debris therefrom, captured by the receptacle cannot passed through the retaining end and into the environment. A wall 62 is disposed between the open end and retaining end for containing the excised heart valve. The aperture 65 provides an edge which forms a cutting edge 66 for excising the heart valve. It also provides an opening through which the excised heart valve enters the receptacle for capture and later compression or compaction.

To perform the cutting function, the cutting edge 66 may be a sharpened end. Additionally or alternatively, it may be disposed with an abrasive or cutting material such as diamond or graphite. Alternatively, or in addition, the cutting edge 66 may be jagged e.g. it may have teeth, triangular, square or otherwise. Preferably, the cutting edge is designed to minimize the about of debris produced. Preferably, the cutting edge is designed to reduce the particle size of debris produced, so that it can be better retained or stored in the receptacle. The ECI preferably is configured for a cutting action which may be a rotation (continuous, intermittent, mono- or bi-directional, or alternative), a linear movement, a combination of these as discussed below.

The receptacle is dimensioned to capture the excised heart valve.

The receptacle formed by the ECI 50 in the open configuration is configured to capture and retain the excised heart valve. Preferably, it can contain the excised heart valve, preventing leakage of debris or particulate matter therefrom into the blood vessel. The wall 62 of the receptacle may form a continuous or discontinuous structure. Where it is formed from a continuous structure (e.g. from abutting or interlocking parts that form a continuous structure), said continuous structure acts as a barrier for the passage of debris or particulate matter. Where the wall is formed from a discontinuous structure, (e.g. from a plurality of struts with intervening openings that form a discontinuous structure) the wall of the receptacle may be disposed with a lining material (e.g. a sheet with a fine mesh). The lining material may be provided whether the wall has a continuous or discontinuous structure. The lining material reduces or prevents the leakage of debris or particulate matter from receptacle void. The lining material is preferably a polymeric fine mesh.

The debris or particulate matter may be calcification particles or pieces of valvular tissues. The particle size considered debris may have a particle size equal to or greater than 0.05 mm, 0.1 mm, 0.2 mm, 0.3 mm, 0.4 mm, 0.5 mm, 0.6 mm, 0.7 mm, 0.8 mm, 0.9 mm, or 1 mm or a value in the range between any two of the aforementioned values, preferably between 0.05 mm and 0.2 mm. The debris size may be determined by standard experimental techniques, such as light scattering. The lining material is provided to allow retention of debris in the receptacle.

To assist with containment of the excised heart valve, the ECB (70, FIG. 5), and more in particular, the support surface 77 of the ECB 70 may co-operate with the receptacle aperture 65 to close the aperture, thereby sealing the excised heart valve within the receptacle. The sealing is typically to the extent that leakage of debris from the excised heart is reduced or prevented. Examples of the sealing co-operation between the ECI 50 and ECB 70 are shown in FIGS. 14 to 21, where FIGS. 14, 16, 18 and 20 illustrate various configurations of a device 100 of the invention where the ECIs 50 and ECBs 70 are separated, and FIGS. 15, 17, 19 and 21 show various configurations of a device 100 of the invention where the respective ECIs 50 and ECBs 70 having been drawn together by the displacement means 5, 6, forming a sealed receptacle.

The ECI 50, 50' may be elongate. The outer shape of the ECI in the open configuration 50 preferably is at least a partly conical, most preferably the shape of a cone truncated at the tip. The wide base of the cone preferably provides the aperture 65, while the tip or truncated tip forms the retaining end of the ECI 50, 50'. Other outer shapes of the ECI in the open configuration 50 are envisaged for instance, cylindrical, barrel, bullet, rivet and the like. The outer shape of the ECI in the closed configuration 50' preferably is preferably cylindrical, but other shapes are envisaged such as barrel, bullet, rivet and the like.

In one embodiment, the ECI 50, 50' is formed from a self-expanding cone. It is preferably formed from a shape memory material such a NiTinol. In the open configuration the self-expanding cone of the ECI forms a conical shape. In the closed configuration, the self-expanding cone of the ECI forms a cylindrical shape. In the native state, no application of force is required to maintain the open configuration. The self-expanding cone is preferably conical in the native state. When a radial force is applied, the self-expanding cone may be moved radially inwards, thereby reducing the diameter of the ECI towards the closed configuration. The cutting edge forms the edge of the apertured opening to the receptacle, while the pivoted end formed the retaining end of the receptacle. Preferably, the plurality of elongate blades is self-expanding into the open configuration.

The self-expanding cone may be made using processes similar to making a self-expanding stents. The self-expanding cone may be made from a flat, perforated structure that is subsequently rolled to form the conical structure that is woven, wrapped, drilled, etched or cut to form passages. The flat structure is typically the arc of an annulus. Self-expanding cone may be braided, from flexible metal, such as special alloys, from NiTinol, or from phynox. Self-expandable cone made from NiTinol may be laser cut.

Figure 7:
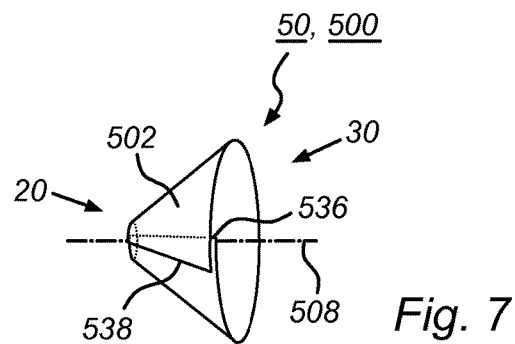
FIG. 7 is a view of an ECI that is an expandable cone.

In one embodiment, depicted for instance in FIG. 7, the ECI 50, 50' comprises an expandable cone 500 having a wall 502 optionally provided with one or more apertures. The expandable cone contains a longitudinal slit that cuts across the cone wall 502. It will be appreciated that the expandable cone has a proximal 20 and distal 30 end, corresponding to the proximal 20 and distal 30 end of the device 100. The longitudinal slit is preferably in the direction of the central axis 508 of the expandable cone. The longitudinal slit preferably extends from the proximal 20 edge to the distal 30 edge of the expandable cone 500. The longitudinal slit is preferably continuous. The longitudinal slit preferably opens the expandable cone 500. Preferably, proximal and distal ends of the expandable cone 500 are not continuous as a result of the longitudinal slit. The longitudinal slit provides two outer side edges 536, 538, which overlap in the open and closed configurations. The edges 536, 538, slide or pivot relative to each other as the cone transitions from the open to the closed state, and vice versa. The expandable cone 500 contracts into the closed configuration by wrapping the wall 502 of the expandable cone 500 into a spiral.

Figure 8:
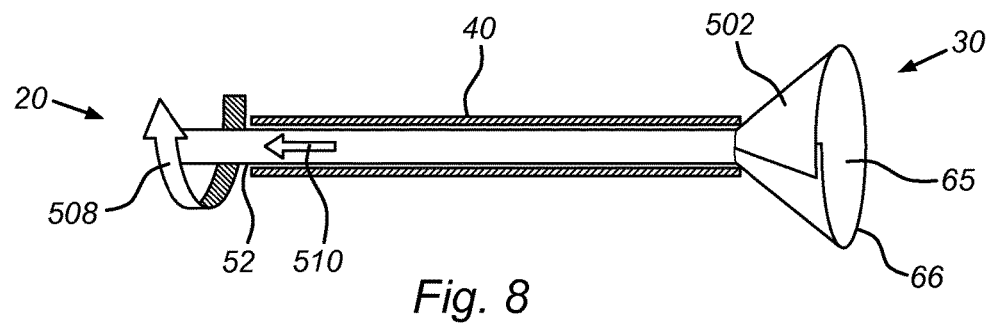
Figure 9:
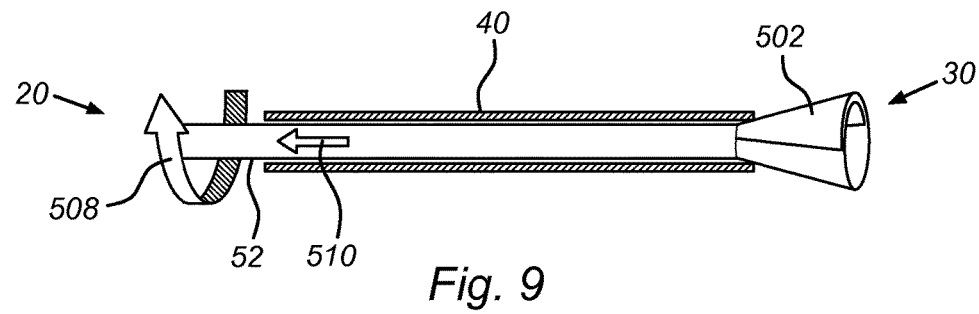
Figure 10:
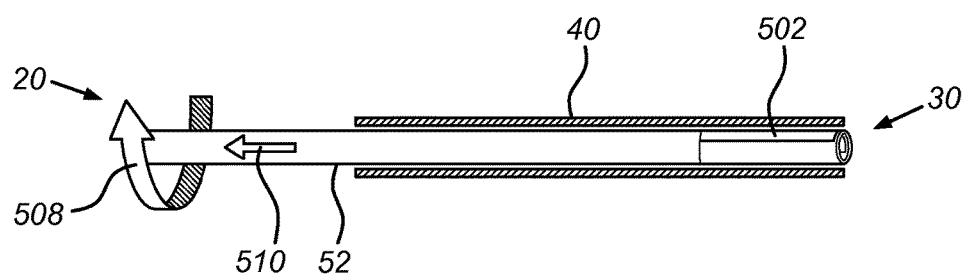

FIGS. 8 to 10 show exemplary stages of transitioning the expandable cone 500 from an open to a closed state. In FIGS. 8 to 10, the ECI 50 that comprises an expandable cone 500 is attached at its narrow end to a first elongate member 52 that is described more fully below. The first elongate member 52 is disposed within a delivery catheter 40. As such the first elongate member 52 forms part of the displacement mechanism. Typically advancement or retraction of the first elongate member 52 is controlled by movements of the first elongate member at the proximal end 20. By rotating 508 and withdrawing 510 proximally the first elongate member 52 relative to the delivery catheter 40 the expandable cone 500 withdraws into the delivery catheter 40. The wall of delivery catheter 40 applies a force to the cone 500, causing the two outer side edges 536, 538 to slide or pivot relative to each other, assisted by rotation 508 of the first elongate member 52. In FIG. 9, the diameter of the cone is reduced, while in FIG. 10, the cone adopts essentially a cylindrical shape and is withdrawn into the delivery catheter 40. The expandable cone 500 is thus configured to transition from the open to closed configuration by rolling the annulus segment into essentially a cylindrical shape, said rolling actuated by the rotation and proximal displacement of the first elongate member 52 relative to the delivery catheter 40. The open configuration of the expandable cone 500 provides the receptacle with a void 64 having an aperture 65 at the distal end. The aperture 65 provides the edge which forms the cutting edge 66 for excising the heart valve. The aperture 65 also provides an opening through which the excised heart valve enters the receptacle for capture and later compression or compaction or folding.

The expandable cone 500 is formed from a material able to transmit the requisite cutting forces to the tissue, and which is able to contract and expand, such as surgical stainless steel or NiTinol. It is appreciated that the use of a shape memory material such as NiTinol, which, in the native state adopts the shape of the (open) cone, would assist in expansion of the expandable cone 500 as it is advanced through the delivery catheter 40.

Figure 11:
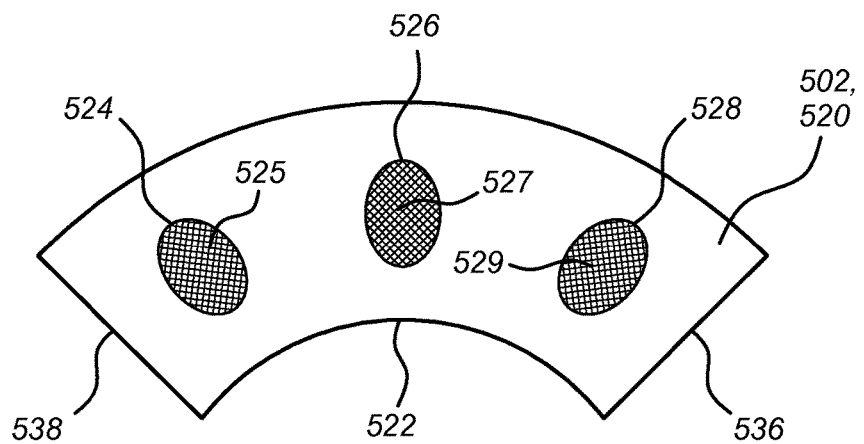
FIGS. 11 and 12 are views of a sheet of material used to form an expandable cone.
Figure 12:
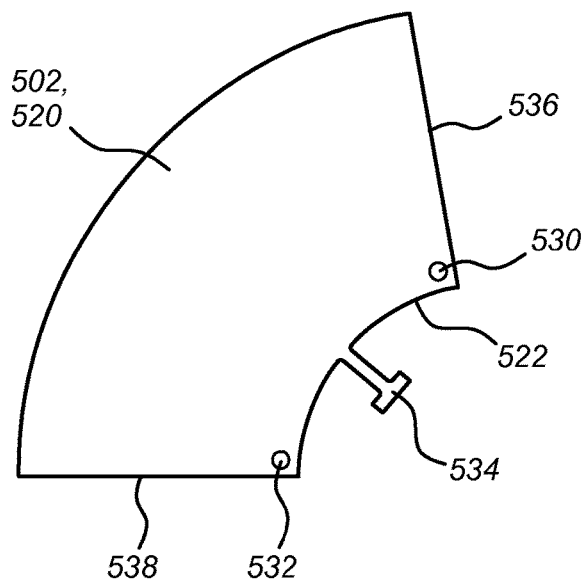

The wall 502 of the expandable cone is preferably formed from a sheet of material 520 comprising a geometric shape that is an annulus segment as depicted in FIGS. 11 and 12. The angle of the segment may be equal to or greater than 60 deg, 65 deg, 70 deg, 75 deg, 80 deg, 85 deg or 90 deg, or a value in a range between any two of the aforementioned values, preferably between 70 and 80 deg, more preferably between 75 deg and 80 deg. The inner annular edge 522 of the sheet—that is the smaller curved (arced) edge—is bent into a circle and attached to the first elongate member 52. The outer annular edge of the sheet—that is the larger (arced) curved edge—forms the cutting edge. The outer side (flanking) edges 536, 538—that is the two edges that the limit the angle of the segment—overlap. In other words, each flanking edge lies adjacent to a wall of the annulus segment. The sheet may contain one or more windows or openings 524, 526, 528, (FIG. 11) thereby giving the wall 502 of the expandable cone 500 windows or openings. These allow fluids to escape during compression or compaction. The windows, or openings, or expandable cone 500 may be disposed with a lining material 525, 527, 529 (e.g. a sheet with a fine mesh). The lining material reduces or prevents the leakage of debris or particulate matter from receptacle void. The lining material is preferably a polymeric fine mesh. The wall 502 of the expandable cone may comprise two holes 530, 532 located adjacent to the outer side edges 536, 538 of the annulus segment and to the inner annular edge 522. When the annulus segment is bent into a cone, the two holes 530, 532 align and act as a pivot point for the expansion (fanning-out) and contraction of the expandable cone 500. The aligned holes 530, 532 may be secured using a rivet or other means. The sheet of material 520 may further be provided with a tab 534 that extends from the inner annular edge 522; such tab may be aligned with a reciprocating groove in the first elongate member 52 to anchor or secure the expandable cone 500 in relation to the first elongate member 52. In addition, or alternatively, the tab may transmit torque. In a preferred embodiment, the tab has a T-shape, the base of the T extending from the inner annular edge 522.

Figure 13:
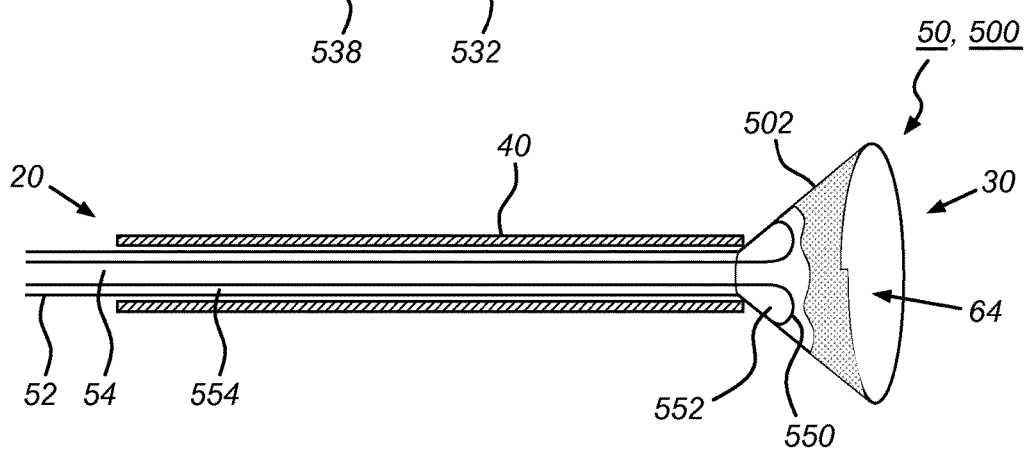
FIG. 13 is a view of an ECI that is an expandable cone, attached to a displacement mechanism, wherein the ECI further comprises an expandable balloon.

Expansion of the expandable cone 500 may be assisted by an ECI expandable balloon 550 as illustrated, for instance, in FIG. 13. The ECI expandable balloon 550 may be disposed in the void 64 at the proximal end 20 of the expandable cone 500 as illustrated, for instance, in FIG. 13. In other words, the ECI 50, 50' may comprise an expandable cone 500 and an ECI expandable balloon 550 configured to expand the expandable cone 500. The ECI expandable balloon preferably has a toroidal shape. The hole of toroid is preferably aligned with the central axis 508 of the expandable cone 500 Such an ECI expandable balloon permits additionally can reinforce the conical shape in the open position and centering of the ECI around the guidewire.

In one embodiment, the ECI 50, 50' is formed from a plurality of elongate blades arranged around a ring, each elongate blade pivoted at one and the same end and provided with a cutting edge at the other end. In the open state the pivoted blades of the ECI form a conical shape. A pivoted blade may take the form of a compliant member fixed at one end in relation to the ring, the blade adopting part of the open conical shape in the native state. A pivoted blade may alternatively take the form of a rigid member fixed at one end in relation to the ring using a hinge joint. In the native state, the hinged blade may adopt a position contributing to the open conical shape using a spring. In the native state, no application of force is required to maintain the open configuration. When a radial force is applied, the pivoted blade may be moved radially inwards, thereby reducing the diameter of the ECI towards the closed configuration. The cutting edge forms the edge of the apertured opening to the receptacle, while the pivoted end formed the retaining end of the receptacle. In the open configuration, the cutting edges may form a continuous ring. Preferably, the plurality of elongate blades is self-expanding into the open configuration.

The ECI 50, 50' may contain a movement limiter (a stop), which restricts the opening of the ECI to a certain size. The limiter may comprise interconnections between adjacent elongate blades. Alternatively, the limiter may comprise loop of variable diameter that passes around the outside of the ECI 50, 50' thereby stopping the ECI 50, 50' from opening past a certain diameter. The diameter may be controlled by the operator from the proximal 20 end, for instance, by feeding a length of wire to the loop "lasso" from the proximal end. Alternatively, the limiter may comprise loop of fixed diameter that passes around the outside of the ECI 50, 50' thereby stopping the ECI 50, 50' from opening beyond a certain diameter. By displacing the loop in a longitudinal manner, the size of the aperture 65 can be controlled by the operator from the proximal 20 end. Alternatively or additionally, the size of the ECI 50 in the open configuration may be set, for instance, by the extent the ECI 50, 50' is advanced forward from the delivery catheter 40 when the ECI 50, 50' is self-expanding; in such case, the terminal tip of the delivery catheter 40 may be provided with a bearing in revolute connection therewith, which bearing revolves around the longitudinal axis of the delivery catheter 40 and has the shape of an annulus. The ECI 50, 50' passes through the hole of the annulus and engages with the bearing upon partial expansion. Thus, rotation of the ECI 50, 50' is transmitted to the bearing, both move synchronously allowing rotation of ECI 50, 50' opened to any diameter relative to the delivery catheter 40.

A blade may be made from any biocompatible material, for instance, stainless steel, titanium, NiTinol, or from a polymeric substance such as polycarbonate.

Figure 22:
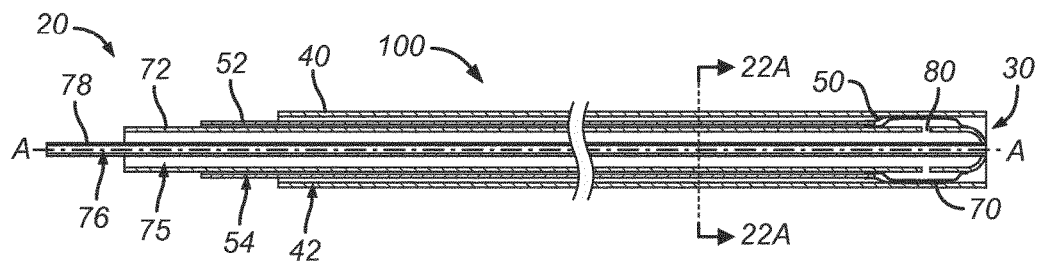
FIG. 22 depicts a longitudinal cross section of a device of the invention comprising an ECI, ECB and displacement mechanism, where the ECI and ECB are in a closed configuration. A longitudinal axis A-A is indicated.

The ECI 50, 50' may be provided attached to a distal end 30 of a first elongate member 5, 52. The first elongate member 52 is configured for advancement or retraction of the ECI through the lumen 42 of a delivery catheter 40. An example of an arrangement of a first elongate member 52 within a delivery catheter 40 and in relation to a second elongate member 72 discussed later below, is shown in FIGS. 22, 29, and 30. As such the first elongate member 52 forms part of the displacement mechanism 5, 6 (in particular reference sign 5 of the pair of elements 5, 6 in FIGS. 14 to 21).

Typically advancement or retraction of the first elongate member 52 is controlled by movements of the first elongate member at the proximal end 20 of the device 100. The ECI 50, 50' is preferably attached to the first elongate member 52 at the distal tip of said member 52.

When the ECI 50, 50' is formed from an expandable cone the expandable cone 500 is attached at its narrow end to a first elongate member 52. When the ECI 50, 50' is formed from a series of elongate blades arranged around a ring, they may be attached at the pivoting end to the first elongate member 52. Preferable a central axis of the first elongate member 52 is co-axial with a central axis 508 of the ECI 50, 50'.

The first elongate member 52 may be disposed with a first elongate member (FEM) instrument lumen 54 that extends from its proximal end 20 to its distal end 30 and is open at both ends. The FEM instrument lumen 54 may be configured for the passage of a second elongate member 70 to which the ECB 70, 70' is operatively attached; this is preferred when the device 100 is used to excise the heart valve via the transapical approach and the cutting edge of the ECI 50 is pointing in the distal 30 direction. In this arrangement, the distal open end of the FEM instrument lumen 54 is in fluid connection with the receptacle void 64. FIGS. 14, 15, 18 and 19 schematically indicate a device 100 having this configuration of elements. FIGS. 22 to 40 also show this arrangement.

Alternatively, first elongate member 52 may be configured for passage through the lumen 74 of a second elongate member 72 to which the ECB 70 is operatively attached; this is preferred when the device 100 is used to excise the heart valve via the transaortic approach and the cutting edge 66 of the ECI 50, 50' is pointing in the proximal 20 direction. FIGS. 16, 17, 20 and 21 schematically indicate a device 100 having this configuration of elements. In this alternative configuration, a lumen of the first elongate member need not be present.

By sliding the first elongate member 52 relative to the second elongate member 72 the distance between the cutting edge 66 and the ECB 70 can be controlled from the proximal end 20 of the device 100. Thus a gap between the cutting edge 66 and the ECB 70 may be set into which the heart valve prior to excision is positioned in situ; this gap may be narrowed during excision, and closed during valve removal.

When the ECI comprises an expandable cone 500 and an expandable balloon 550, the first elongate member 52 may be disposed with a first elongate member (FEM) first inflation lumen 554 from its proximal end to its distal end. The expandable balloon 550 comprises a lumen 552 that is fluidicly connected to the FEM first inflation lumen 554 as illustrated, for instance, in FIGS. 13, 29 and 30. The first elongate member 52 may be disposed with a FEM first inflation lumen 554 from its proximal end to its distal end.

The FEM first inflation lumen 554 may be configured for the passage of inflation fluid (e.g. saline) from a pump in fluid connection with the first inflation lumen at the proximal end of the first elongate member 52. Inflation fluid is used to inflate the expandable balloon 550 comprised in the ECI 50, 50'. Preferably, the FEM first inflation lumen 554 is sealed at the distal 30 end, preferably by connection with the expandable balloon 550, preventing the seepage of inflation fluid from the distal end of the first elongate member 52. Where the expandable balloon 550, has a toroidal shape, the hole of the toroid is preferably aligned with the FEM first instrument lumen 54. The hole of toroid allows the passage of the second elongate member 72 and also the ECB 70 therethrough. Where a FEM first instrument lumen 54 and FEM first inflation lumen 554 are both present in the first elongate member 52, it is preferred that the FEM first inflation lumen 554 surrounds the FEM first instrument lumen 54.

The first elongate member 52 may also be provided with a FEM guidewire lumen. The FEM guidewire lumen facilitates advancement of the device and delivery catheter over a guidewire. The FEM guidewire lumen may be configured for advancement of the device 100 in an over-the-wire or in a rapid-exchange mode of operation. The FEM guidewire lumen is typically a tube or tubular cavity disposed within the first elongate member 52. Preferably, the FEM guidewire lumen is for an over-the wire operation and extends from the proximal 20 to the distal 30 end of the first elongate member 52; it is preferably open at both ends. The first elongate member 52 may incorporate a distal tip, through which the FEM guidewire lumen extends. The distal tip may be softened and atraumatic.

The outer wall of the first elongate member 52 may be formed using an extrusion process or non-extrusion process. The outer wall of the first elongate member 52 may be formed from a biocompatible material which provides the requisite flexibility, pushability and strength. Suitable biocompatible materials include, but are not limited to a polymer such as polypropylene, polyethylene, polyurethanes, polyamide, polyimide poly(ethylene terephthalate) (PET) or polyesters and copolymers thereof, metal (stainless steel, NiTinol) of a combination of metal and polymer. In a preferred embodiment it is formed from a polymeric material that is polyamide, polyimide, stainless steel or NiTinol or a combination or blend of these. The outer wall of the first elongate member 52 may be formed from a polymeric material (e.g. polyimide) strengthened with braided or coiled metal (stainless steel or NiTinol) disposed within the polyimide wall. For a first elongate member 52 formed by extrusion, it is preferably formed from polyamide. For a first elongate member 52 formed by non-extrusion, it is preferably formed from polyimide. The exterior may be coated to reduce friction during insertion or withdrawal. Example of a suitable friction-reducing coating includes Teflon.

According to a particular aspect of the invention, a first elongate member 52 which passes through the void 64 of the receptacle formed by the ECI 50 in the open configuration may contain a compressible wall i.e. in a sub-region of a first elongate member 52 that occupies the void 64. A compressible wall provides a larger effective void 64 volume for retaining and compressing or compacting the excised valve. For instance, the first elongate member 52 may pass through the void 64 of the receptacle formed by the ECI 50 in the open configuration; this is particularly the case when the cutting edge 66 of the ECI 50 is pointing in a proximal 20 direction as shown, for instance, in FIGS. 16 and 20, and the device is used for the transaortic approach. A sub-region of wall of the first elongate member 52 that occupies the void 64 may be compressible, preferably radially compressible.

The ECI 50, 50' and ECB 70, 70' are oriented such that the ECB support surface 77 and the ECB cutting edge 66 are mutually adjacent.

The ECI 50, 50' may be orientated such that the cutting edge 66 is pointing in the distal direction 30; this is preferable when the ECB support surface is pointing in the proximal direction 20. Such arrangement is preferred when the device 100 is used to excise the heart valve via the transapical approach. FIGS. 14, 15, 18 and 19 schematically indicate a device 100 of the invention having this configuration of elements.

Alternatively, the ECI 50, 50' may be orientated such that the cutting edge 66 is pointing in the proximal direction 20; this is preferable when the ECB support surface 77 is pointing in the distal direction 30. Such arrangement is preferred when the device is used to excise the heart valve via the transaortic approach. FIGS. 16, 17, 20 and 21 schematically indicate a device 100 of the invention having this configuration of elements.

The ECI 50, 50' may be configured for rotation around an axis that is preferably its central (longitudinal) axis. Rotation of the ECI provides a rotating blade at the cutting edge 66 which results in a more efficient excision that may require less force compared with merely punching-out the defective heart valve. The ECI may be held in fixed relation to the first elongate member such that rotation of the cutting edge 66 can be actuated by rotation of the first elongate member 52 at the proximal end 20. The rotation may be motorized, for example, by attachment of the drive shaft of an electric motor to the proximal end 20 of the first elongate member 52. Preferably, ECI 50, 50' configured for rotation relative to the ECB 70, 70' and relative to the delivery catheter 40 i.e. the ECB 70, 70' and delivery catheter 40 remain rotationally static. The rotation may be clockwise, counter-clockwise, or may oscillate between the clockwise and counter-clockwise directions.

It will be appreciated that other cutting actions, besides rotation, can be utilised, such as a linear displacement in a longitudinal direction. For instance, the cutting action may be an oscillation in the longitudinal direction that rapidly advances and withdraws the cutting edge, to provide a hammering action. It will be appreciated that the rotation and hammering action may be combined.

The ECI 50, 50', or more properly the receptacle formed in the open configuration is configured to compress or compact the excised heart valve after capture. The compression or compaction may be radial. Compression or compaction may be achieved, for instance, by withdrawal of the ECI 50, 50' in the open configuration into the delivery catheter lumen. The cross-sectional area of the delivery catheter lumen is smaller than the maximum cross-sectional area of the receptacle, thus radial pressure is applied to the receptacle as it is withdrawn into the restricting luminal space. The result is the excised heart valve is crushed and compacted. The excised heart valve may be stored in the lumen of the delivery catheter at the distal end, until the delivery catheter is withdrawn from the heart.

The wall of such a delivery catheter is typically made from a material that is resistant to radial expansion (see below).

When the ECI is formed, as mentioned elsewhere herein, from an expandable cone, or from a plurality of elongate blades arranged around a ring, pivoted at one end, and the blades or cone is made from a rigid material that is resistant to bending in the direction of the central axis, the blades or cone acts as a lever to transmit compression forces. Forces increase as the ECI is withdrawn into the delivery catheter lumen.

The use of a lever system implemented through the cone or elongate blades compresses or compacts the heart valve material, effectively reshaping it into a cylindrical form for withdrawal through the delivery catheter. As the valve tissue itself is effectively incompressible owing to calcification, the compression or compaction utilised in the invention reduces the spaces between valve leaflets, and effectively molds the valve into a new form. The ECB effectively assists in the folding of the excised valve by pushing it, or a part of it, inside the ECI and/or by applying forces to assist its folding. Example 2 below shows the effect of the compression forces applied by the receptacle in reshaping the valve into a withdrawable cylindrical form.

The ECI 50 may be provided with one or more radio-opaque markers. Preferably at least one marker is provided on or adjacent to the cutting edge 66. Radio-opaque substances are well known in the art, and include barium, barium impregnated polymers (e.g. barium impregnated polythene) and the like, metals or other materials with specific density permitting the visualization without significant artifacts.

Figure 2:
FIG. 2 is a schematic view of an expandable cutting block (ECB) in a closed configuration.
Figure 5:
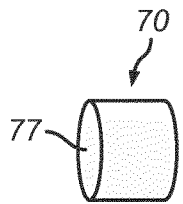
FIG. 5 is a schematic view of an ECB in an open configuration.

With reference to FIGS. 2 and 5, the ECB has a closed 70' and open 70 configuration. In the closed configuration, the ECB 70' has a narrower profile compared with the ECB 70 in the open configuration. In the closed configuration, the ECB 70' is able to pass substantially unhindered through the lumen of the delivery catheter. The ECB is capable of expanding from a closed configuration 70' to an open configuration 70; this is typical for deployment of the ECB through a catheter where the ECB remains closed while the delivery catheter is advanced, and expands during deployment. The ECB is also capable of contracting from an open configuration 70 to a closed configuration 70'; this is typical when ECB is withdrawn back into the catheter. The ECB may assist with the closure of the ECI during compression or compaction of the excised valve. Preferably in the closed configuration the ECB 70' has a maximum outer transverse-cross-sectional diameter of 0.1 cm, 0.2 cm, 0.3 cm, 0.4 cm, 0.5 cm, 0.6 cm, 0.7 cm, 0.8 cm 0.9 cm, 1 cm or a value in the range between any two of the aforementioned values, preferably between 0.8 to 1 cm, most preferably about 0.9 cm.

Preferably in the opened configuration the ECB 70 has a maximum outer transverse-cross-sectional diameter of 2.0 cm, 2.2 cm, 2.3 cm, 2.4 cm, 2.5 cm, 2.6 cm, 2.7 cm, 2.8 cm, 2.9 cm, or 3.0 cm or a value in the range between any two of the aforementioned values, preferably between 2.4 to 2.6 cm, most preferably about 2.5 cm.

The ECB 70, 70' may be radially expandable. Alternatively, the ECB 70, 70' may be non-radially expandable. The ECB 70, 70' may be longitudinally expandable. Alternatively, the ECB may be non-longitudinally expandable. Preferably, the ECB 70, 70' is radially expandable and non-longitudinally expandable.

It is preferred that the ECB 70, 70' is manually expandable and contractible, for instance, is formed from an expandable balloon.

Alternatively, the ECB 70, 70' may be self-expanding from the closed state to the open state; in other words, when it is sheathed using a constricting over-sheath, the ECB is in a closed configuration. When the ECB is unsheathed, the ECB expands to the open configuration. Such a sheath may be formed from the first elongate member 52 provided with a lumen 54. Alternatively, such a sheath may be formed from a delivery catheter 40 provided with a lumen 42 (see FIG. 22).

Expansion and/or contraction of the ECB 70, 70' may be actuated by an expansion mechanism. Such mechanism which may utilize an expandable balloon, sheathing/unsheathing, or the like.

The ECB 70 in the open configuration may serve to position the device 100 at its distal end correctly in situ over the heart valve to be excised. As it expands, it contacts the vessel wall, which forces the distal end of the device 100 into a position that centers the ECB over the heart valve. In particular, the centering function may orientate and/or align the longitudinal axis of the ECB with a longitudinal axis the aortic valve. In particular, it may align the longitudinal axis of the ECB with a central axis of the aortic valve ring, wherein the aortic valve ring represents aortic valve perimeter junction with the aorta. The ECB 70 in the open configuration aligns the ECB 70 with the aorta, and the ECB 70 also aligns the ECI 50 such that the cutting edge 66 is aligned with the support surface 77.

In the open configuration the ECB 70, also serves to anchor the device 100 against the wall of the vessel.

The ECB 70 in the open configuration provides a support surface 77 for supporting the heart valve during excision by the ECI (FIG. 5). The support surface 77 receives the heart valve, and forces applied to said valve during excision. It effectively acts as a cutting block or anvil. To prevent movement of the heart valve during excision, the support surface 77 may be provided with a friction surface that frictionally engages the valve. The friction surface may comprise a plurality of protrusions e.g. dimples, pins, serrations which engage with and lock the heart valve in position. Alternatively or additionally, the friction surface may be provided with a friction-enhancing coating.

The support surface 77 has a profile that at least matches the profile of the cutting edge 66. Preferably it has a circular shape, preferably it has an annular shape.

Optionally, a complementing receptacle may be formed by the ECB 70 in the open configuration. In other words, the ECB may be hollow, the hollow forming a void of the complementing receptacle. The complementing receptacle contains at one end an aperture, giving access to the void. At the other end, the receptacle is preferably closed from open access to the environment (retaining end). A wall is disposed between the open end and retaining end for containing the excised heart valve or a part thereof. It also provides an opening through which the excised heart valve enters the receptacle for capture and later compression or compaction. The complementing receptacle is dimensioned to capture the excised heart valve. The complementing receptacle feature of the ECB 70 is particularly evident when the support surface has an annular (ring) shape, the hole of the annular ring forming the aperture of the ECB 70. When the ECB 70 and ECI 50 are moved into contact each other, by virtue of the displacement mechanism 5, 6, the respective apertures co-operate, and a combined void is formed from the respective voids. The combined void has a larger volume than the ECI void 64 alone. The combined void permits an optimised distribution of the native valve and debris therefrom in the ECB 70 void, in the ECI 50 void or both. The cutting blades and/or cutting edge of the ECI 50 may be configured to facilitate the optimised distribution.

When the ECB 70 and ECI 50 are moved into contact each other, by virtue of the displacement mechanism 5, 6, the ECB 70 covers the aperture 65 of the ECI, thereby sealing the receptacle void. Accordingly, debris from the excised heart valve is effectively contained in a sealed container. The combined ECB 70 and ECI 50 elements may be subsequently contacted and withdrawn into the delivery catheter 40.

The ECB 70, 70' may be elongate. The outer shape of the ECB 70 in the open configuration preferably is at least a partly cylindrical, most preferably having rounded ends. Other outer shapes of the ECB 70 in the open configuration are envisaged for instance, conical, barrel, bullet, rivet and the like. The support surface is formed at one longitudinal end of the ECB and preferably contacts a plane that is substantially perpendicular to the central axis of the ECB 70, 70'. Where the ECB 70 forms a receptacle in the open configuration, the ECB may have a three dimensional shape that is a beaker, the rim of the beaker forming the support surface 77.

According to a preferred aspect, the ECB 70 comprises an inflatable balloon, that inflates to a suitable shape and dimension to provide the support surface 77. The balloon comprises a balloon wall and an interior balloon lumen configured to receive inflation fluid. The balloon wall may be made from any suitable elastomeric polymer material having moisture impermeable properties, able to withstand inflation pressure, such as polyamide (e.g. PA11, PA12), nylons, PEBAX™, polyethylene, latex rubber, elastic, or plastic. The support surface 77 of the inflatable balloon may be provided with a friction surface that frictionally engages the valve. The friction surface may comprise a plurality of protrusions e.g. dimples, pins, serrations which engage with and lock the heart valve in position. Alternatively or additionally, the friction surface may be provided with a friction-enhancing coating. The balloon is preferably elongate, and essentially cylindrical in the open configuration.

According to one aspect, the inflatable balloon is inflatable in two stages or more precisely to two different volumes. At a first inflation stage, the inner inflatable balloon inflates to a suitable shape and dimension to provide to position the device 100 at its distal end correctly in situ over the heart valve to be excised. As inner inflatable balloon expands, it contacts the vessel wall, which forces the distal end of the device 100 into a position that centers the ECB over the heart valve. In particular, the centering function of the inner inflatable balloon may orientate and/or align the longitudinal axis of the ECB with a longitudinal axis the aortic valve. In particular, it may align the longitudinal axis of the ECB with a central axis of the aortic valve ring, wherein the aortic valve ring represents aortic valve perimeter junction with the aorta. Once positioned and centered, the balloon is further inflated to a second stage to provide the support surface 77. After the resection, the deflation of the balloon to the first stage permits displacement of the ECB and ECI and continued sealing receptacle formed in the ECI.

According to one aspect, the ECB 70 comprises two inflatable balloons, an inner inflatable balloon and an outer inflatable balloon. The inner inflatable balloon is disposed within a lumen of the outer inflatable balloon. The inner and outer balloons may be independently inflatable. Alternatively, the outer balloon may inflate only after the inner balloon has been inflated. The inner inflatable balloon inflates to a suitable shape and dimension to provide to position the device 100 at its distal end correctly in situ over the heart valve to be excised. As inner inflatable balloon expands, it contacts the vessel wall, which forces the distal end of the device 100 into a position that centers the ECB over the heart valve. In particular, the centering function of the inner inflatable balloon may orientate and/or align the longitudinal axis of the ECB with a longitudinal axis the aortic valve. In particular, it may align the longitudinal axis of the ECB with a central axis of the aortic valve ring, wherein the aortic valve ring represents aortic valve perimeter junction with the aorta. Once positioned and centered, the outer balloon may be inflated to provide the support surface 77. After the resection, the deflation of the outer balloon permits displacement of the ECB and ECI, while the inner balloon may stay inflated and continue sealing receptacle formed in the ECI.

The ECB 70 may be provided attached to a distal end 30 of a second elongate member 72. The second elongate member 72 is configured for advancement or retraction of the ECB through the lumen 42 of a delivery catheter 40. An example of an arrangement of a second elongate member 72 within a delivery catheter 40 and in relation to the first elongate member 52 discussed later below, is shown in FIG. 22. As such the second elongate member 72 forms part of the displacement means 5, 6 (in particular reference sign 6 of the pair of elements 5, 6 in FIGS. 14 to 21). Preferably, a central axis of the second elongate member 72 is co-axial with a central axis of the ECB 70.

Typically, the ECB 70, 70' is controlled via the second elongate member 72 responsive to movements at the proximal end 20. In particular, advancement or retraction of the second elongate member 72 is controlled by movements of the second elongate member at the proximal end 20. As such the second elongate member 72 forms part of the displacement mechanism 5, 6.

The second elongate member 72 may be configured for passage through the FEM instrument lumen 54 of a first elongate member 52 to which the ECI 50, 50' is operatively attached; this is preferred when the device 100 is used to excise the heart valve via the transapical approach and the support surface 77 of the ECB 70, 70' is pointing in the proximal direction. FIGS. 14, 15, 18 and 19 schematically indicate this configuration of elements. FIGS. 22 to 40 also show this arrangement.

Alternatively, the second elongate member 72 may be disposed with a second elongate member (SEM) instrument lumen from its proximal end to its distal end, open at both ends. The SEM instrument lumen may be configured for the passage of the first elongate member 52 to which the ECI 50, 50' is operatively attached; this is preferred when the device 100 is used to excise the heart valve via the transaortic approach and the support surface 77 of the ECB is pointing in the distal 30 direction FIGS. 16, 17, 20 and 21 schematically indicate this configuration of elements. In this alternative configuration, a FEM instrument lumen 52 need not be present.

When the ECB 70, 70' is formed from a balloon, as shown, for instance, in FIGS. 22 to 28 the balloon is attached to the distal end of the second elongate member 72, and a balloon lumen is in fluid communication with a second elongate member (SEM) first inflation lumen 74 of the second elongate member 72. In FIG. 20 the balloon lumen and SEM first inflation lumen 74 are connected using a port 80.

As mentioned, the second elongate member 72 may be disposed with a SEM first inflation lumen 74 from its proximal end to its distal end. The SEM first inflation lumen may be configured for the passage of inflation fluid (e.g. saline) from a pump in fluid connection with the first inflation lumen at the proximal end of the second elongate member. Inflation fluid is used to inflate the ECB when it is a balloon. Preferably, the SEM first inflation lumen 74 is sealed at the distal 30 end, preventing the seepage of inflation fluid from the distal end of the second elongate member.

When the ECB 70, 70' is formed from two balloons 71, 71', as shown, for instance, in FIG. 30 the balloons are attached to the distal end of the second elongate member 72. An inner balloon lumen is in fluid communication with a second elongate member (SEM) inner-balloon inflation lumen 74 of the second elongate member 72. In FIG. 30 the balloon lumen and SEM inner-balloon inflation lumen 74 are connected using a port 80. An outer balloon lumen is in fluid communication with a SEM outer-balloon inflation lumen 73 of the second elongate member 72. In FIG. 30 the balloon lumen and SEM outer-balloon inflation lumen 73 are connected using a port 84. The second elongate member 72 may be disposed with a SEM inner-balloon inflation lumen 74 from its proximal end to its distal end, and with a SEM outer-balloon inflation lumen 73 from its proximal end to its distal end The SEM inner- and outer-balloon inflation lumens may be configured for the passage of inflation fluid (e.g. saline) from a pump in fluid connection with the first inflation lumen at the proximal end of the second elongate member. Inflation fluid is used to inflate the ECB when it is a balloon. Preferably, the SEM inner—74 and outer—73 balloon inflation lumens is sealed at the distal 30 end, preventing the seepage of inflation fluid from the distal end of the second elongate member.

The second elongate member 72 may also be provided with a SEM guidewire lumen; this is particularly when the device 100 is configured for the transapical approach. The SEM guidewire lumen facilitates advancement of the device 100 and delivery catheter over a guidewire. The SEM guidewire lumen may be configured for advancement of the device 100 in an over-the wire or in a rapid-exchange mode of operation. The SEM guidewire lumen is typically a tube disposed within the inflation lumen 74 of the second elongate member 72. Preferably, the SEM guidewire lumen is for an over-the wire operation and extends from the proximal 20 to the distal 30 end of the second elongate member 72; it is preferably open at both ends. Preferably, the SEM guidewire lumen is fluidicly isolated from the SEM first inflation lumen 74. An example of a guidewire lumen for an over-the-wire mode is shown in FIG. 22, in which the SEM guidewire lumen 76 defined by a tube 78 is disposed within the SEM first inflation lumen 74, and is open is both ends. The second elongate member 72 may incorporate a distal tip, through which the SEM guidewire lumen 76 extends. The distal tip may be softened and atraumatic.

The outer wall of the second elongate member 72 may be formed using an extrusion process or non-extrusion process. The outer wall of the second elongate member 72 may be formed from a biocompatible material which provides the requisite flexibility, pushability and strength. Suitable biocompatible materials include, but are not limited to a polymer such as polypropylene, polyethylene, polyurethanes, polyamide, polyimide poly(ethylene terephthalate) (PET) or polyesters and copolymers thereof, metal (stainless steel, NiTinol) of a combination of metal and polymer. In a preferred embodiment it is formed from a polymeric material that is polyamide, polyimide, stainless steel or NiTinol or a combination or blend of these. The outer wall of the second elongate member 72 may be formed from a polymeric material (e.g. polyimide) strengthened with braided or coiled metal (stainless steel or NiTinol) disposed within the polyimide wall. For a second elongate member 72 formed by extrusion, it is preferably formed from polyamide. For a second elongate member 72 formed by non-extrusion, it is preferably formed from polyimide. The exterior may be coated to reduce friction during insertion or withdrawal. Example of a suitable friction-reducing coating includes Teflon.

According to a particular aspect of the invention, a second elongate member 72 which passes through the void 64 of the receptacle formed by the ECI 50 in the open configuration may contain a compressible wall i.e. in a sub-region that occupies the void 64. A compressible wall provides a larger effective void 64 volume for retaining and compressing or compacting the excised valve.

For instance, the second elongate member 72 may pass through the void 64 of the receptacle formed by the ECI 50 in the open configuration; this is particularly the case when the cutting edge 66 of the ECI 50 is pointing in a distal 30 direction as shown, for instance, in FIGS. 16, 20, 22, 23 to 29, 30, 31 and 32 to 40, and the device is used for the transapical approach. The wall of the second elongate member 72 contains a sub-region that occupies the void 64 and the subregion is compressible, preferably radially compressible.

The ECI 50, 50' and ECB 70, 70' are oriented such that the ECI support surface 77 and the ECB cutting edge 66 are mutually adjacent.

The ECB may be orientated such that the support surface is pointing in the proximal direction; this is preferable when the ECI cutting edge is pointing in the distal direction. Such arrangement is preferred when the device 100 is used to excise the heart valve via the transapical approach. FIGS. 14, 15, 18 and 19 schematically indicate this configuration of elements.

Alternatively, the ECB 70, 70' may be orientated such that the support surface 77 is pointing in the distal 30 direction; this is preferable when the ECI cutting edge 66 is pointing in the proximal 20 direction. Such arrangement is preferred when the device 100 is used to excise the heart valve via the transaortic approach. FIGS. 16, 17, 20 and 21 schematically indicate this configuration of elements.

The ECB 70 may be provided with one or more radio-opaque markers. Preferably at least one marker is provided on or adjacent to the support surface 77. Radio-opaque substances are well known in the art, and include barium, barium impregnated polymers (e.g. barium impregnated polythene) and the like, metals or other materials with specific density permitting the visualization without significant artifacts.

As mentioned elsewhere, the device is provided with a displacement mechanism 5, 6 (FIGS. 14 to 21) for adjusting the distance between the cutting edge 66 and the ECB 70. The displacement mechanism 5, 6 is preferably realized by the arrangement of first 52 and second 72 elongate members attached to the ECI 50 and ECB 70 respectively, which allow adjustment of the relative position of the ECI 50 and ECB 70 by control at the proximal end of the device 100.

The first 52 and second 72 elongate members are slidable with respect to each other. The first 52 and second 72 elongate members are independently slidable with respect to the delivery catheter 40. The first 52 and second 72 elongate members are preferably in co-axial alignment. The first 52 and second 72 elongate members may be in a non-co-axial alignment e.g. side-by-side. The sliding of first 52 and second 72 elongate members may be actuated manually (e.g. by the surgeon's manipulation) or automatically (e.g. using an electrical, or pneumatic motor) from the proximal end.

A delivery catheter 40 may be provided to deliver the ECI 50, 50' and ECB 70, 70' to the site of treatment. The delivery catheter comprises an elongated shaft 30 (also referred to as a shaft herein) having a proximal end 20 and a distal end 30. The shaft may form the wall of delivery lumen 42. The proximal 20 and distal 30 terminal ends of the delivery lumen 42 are open. The elongated shaft is tubular, typically cylindrical, having a generally uniform outer shape in the proximal region. It will be appreciated that an open proximal end may be configured for connection to one or more hubs. One or more hubs such as a Y-type connector, optionally with Luer fittings may be fitted to the proximal terminal end of the shaft to facilitate passage of the first 52 and second 72 elongate members, guidewire, and coupling to equipment for providing inflation fluid to an inflation lumen, equipment to provide torque/longitudinal force via the first elongate member to the ECI, equipment to provide longitudinal force via the second elongate member to the ECB. Such a hub may be a fluid delivery coupling as described elsewhere herein, which includes hemostatic valve as described, for instance, in U.S. Pat. No. 5,195,980 and which is incorporated herein by reference.

As would be understood by those of skill in the art, the shaft 30 may preferably be sized for slidable passage through, for example, the working channel of an endoscope or through a body lumen, in particular vasculature (through an introducer). As a general guidance, for vascular applications, the maximum outer diameter of the shaft 30 towards the distal (in situ) end may be equal to or no greater than 30 F (10 mm), 31 F (10.33 mm), 32 F (10.66 mm), 33 F (11 mm), 34 F (11.33 mm), 35 (11.66 mm), 36 F (12 mm), 37 F (12.33 mm), 38 F (12.66 mm), 39 F (13 mm), 40 F (13.33 mm) a value in the range between any two of the aforementioned values, preferably between 30 F (10 mm) and 40 (11.33 mm), more preferably about 33 F (11 mm).

As a general guidance, the maximum inner diameter of the delivery lumen 42 towards the distal (in situ) end may be equal to or no greater than 6 mm, 7 mm, 8 mm, 9 mm, 10 mm, or 11 mm, 12 mm, or 13 mm or a value in the range between any two of the aforementioned values, preferably between 6.66 mm and 11 mm, more preferably about 10.66 mm.

The shaft of the delivery catheter 40 may be formed using an extrusion process or non-extrusion process. A shaft may be formed from a biocompatible material which provides the requisite flexibility, pushability and strength. The may also exhibit low or no radial expansion when it is used to deploy a self-expanding element such as a self-expanding ECI 50. Suitable biocompatible materials include, but are not limited to a polymer such as polypropylene, polyethylene, polyurethanes, polyamide, polyimide poly(ethylene terephthalate) (PET) or polyesters and copolymers thereof, metal (stainless steel, NiTinol) of a combination of metal and polymer. In a preferred embodiment it is formed from a polymeric material that is polyamide, polyimide, stainless steel or NiTinol or a combination or blend of these. The shaft may be formed from a polymeric material (e.g. polyimide) strengthened with braided or coiled metal (stainless steel or NiTinol) disposed within the polyimide wall. For a shaft formed by extrusion, it is preferably formed from polyamide. For a shaft formed by non-extrusion, it is preferably formed from polyimide. The exterior may be coated to reduce friction during insertion or withdrawal. Example of a suitable friction-reducing coating includes Teflon.

Figure 22A:
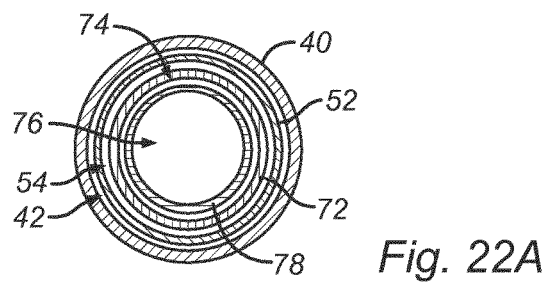
FIG. 22A depicts a transverse cross section of a device depicted in FIG. 22 along a plane indicated by the line in FIG. 22.

An example of device 100 of the invention comprising an ECI 50 and ECB 70 is shown in FIGS. 22 and 22A. The device is suitable excision via the transapical approach. A delivery catheter 40 is indicated, provided with a lumen 42 (delivery lumen) extending from the proximal to the distal end, that is open at both proximal 20 and distal 30 ends. Disposed in the delivery lumen 42 and in slidable relation thereto is a first elongate member 52 to which a self-expanding ECI 50 is attached to its distal tip. The first elongate member 52 is provided with a separate lumen 54 extending from the proximal to the distal end, that is open at both proximal 20 and distal 30 ends. The distal open end of the first elongate member 52 lumen 54 passes into or through the ECI 50 void 64. Disposed in this separate lumen 54 and in slidable relation thereto is a second elongate member 72 to which an ECB 70 is attached to its distal end. The ECB 70 comprises an inflatable balloon. The second elongate member 72 is provided with a first inflation lumen 74, extending from the proximal to the distal end, that is open at the proximal 20 end and closed (sealed) at the distal 30 end. The first inflation lumen 74 is in fluid connection with a lumen of the inflatable balloon via a connecting port 80. The second elongate member 72 is further provided with a guidewire lumen 76, extending from the proximal to the distal end, that is open at both proximal 20 and distal 30 ends. The guidewire lumen is defined by a tube 78 disposed within the first inflation lumen 74. The guidewire lumen 76, first inflation lumen 74, and first elongate member lumen 54 are arranged within the delivery catheter lumen 42 in a substantially co-axial alignment (FIG. 22A), with the first inflation lumen 74 surrounding the guidewire lumen 76. However, it is equally within the scope of the invention that the lumens 74, 76 of the second elongate member 72 are in a side-by-side configuration.

Figure 25:
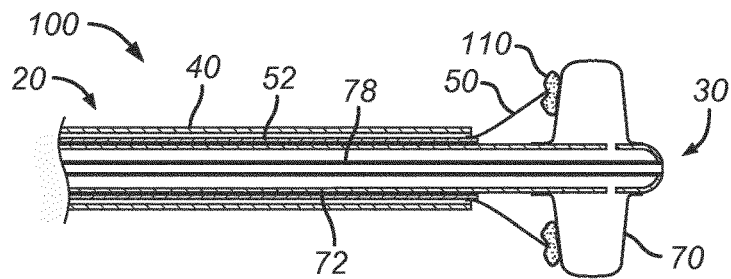
Figure 26:
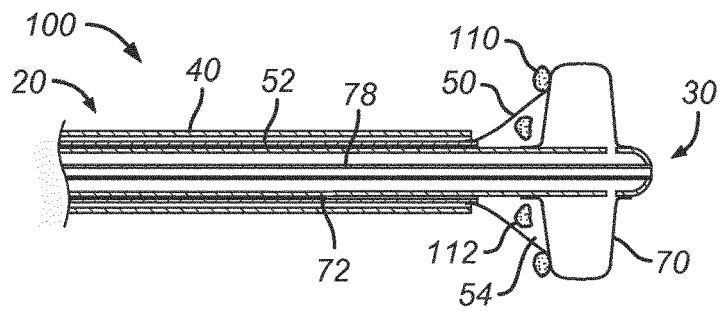
Figure 27:
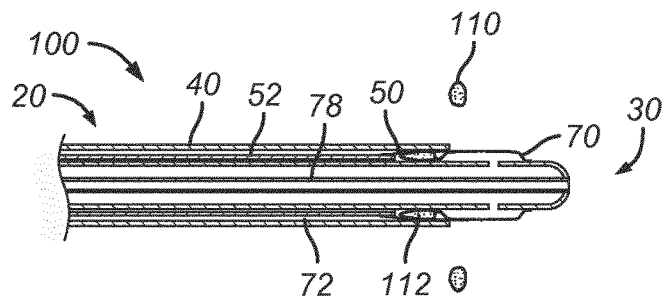
Figure 28:
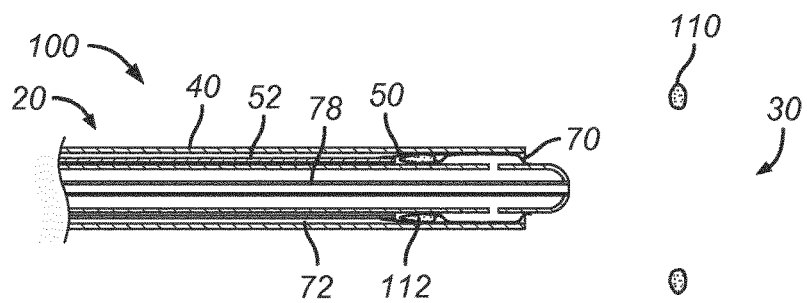

An illustration of a device 100 of the invention in use is provided in FIGS. 22 to 28 and described as follows. After delivery of the sheathed device 100 (FIG. 22) to the site of treatment, the ECI 50 is unsheathed (FIG. 23) and expanded by advancement of the first elongate member 52 relative to the delivery catheter 40 from the proximal end 20. The ECI 50 is self-expanding, and formed from a plurality of hinged blades that constitute a truncated cone in the open configuration. The ECB 70—which comprises a balloon—is also advanced distally relative to the delivery catheter 40 responsive to movement of the second elongate member 72 at the proximal end 20. Once the ECB 70 is put into position, it is inflated (FIG. 24); inflation centres the device 100, in particular the ECI 50, and anchors the ECB 70 relative to the vessel wall 110. The ECI 50 in the open configuration, having a cutting edge is advanced distally 30 towards the ECB 70 (FIG. 25). The heart valve, supported by the ECB 50 is excised using the cutting edge of the ECI 50; excision is assisted by rotation of the first elongate member 52 which transmits torque to the cutting edge. The excised valve 112 is captured in the void 64 formed by the open configuration of the ECI 50 (FIG. 26), and is retained by the lid formed by the supporting surface of the ECB 70. The first 52 and second 72 elongate members are retracted into the distal 30 end of the delivery catheter 40 (FIG. 27). Concomitantly, the excised valve 112 is compressed or compacted by radial forces acting on the blades of the ECI 50, applied during withdrawal of the first elongate member 52. The excision procedure may be assisted by one or more radio-opaque markers present on the ECI 50 and/or ECB 70. The markers may indicate, for instance, when the ECI 50 and ECB 70 flank the heart valve.

The device of the invention may further comprise an implant delivery unit (IDU), for delivery of the replacement heart valve (RHV) after removal of the heart valve. The IDU comprises a RHV. The IDU is capable of expansion from a closed configuration to an open configuration. The IDU may also be capable of contraction from an open configuration to a closed configuration.

Figure 3:
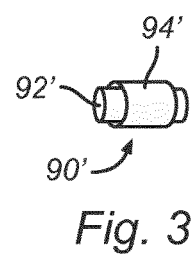
FIG. 3 is a schematic view of an implant deployment unit (IDU) in a closed configuration.
Figure 6:
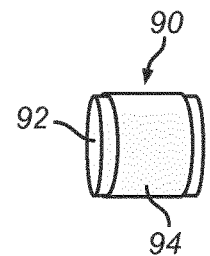
FIG. 6 is a schematic view of an IDU in an open configuration.

With reference to FIGS. 3 and 6 wherein the IDU comprises a balloon 92, 92' and a balloon expandable RHV 94, 94', the IDU has a closed 90' and open 90 configuration. It will be appreciated that the invention is not limited to this configuration; the IDU may take any form, for instance comprise a self-expanding RHV, avoiding the requirement for a balloon. In the closed 90' configuration, the IDU has a narrower profile compared with the IDU in the open 90 configuration. In the closed 90' configuration, the IDU is able to pass substantially unhindered through the lumen of the delivery catheter. The IDU is capable of expanding from a closed 90' configuration to an open 50 configuration; this is typical for deployment of the IDU through a delivery catheter where the IDU remains closed while the delivery catheter is advanced, and expands during deployment. The IDU is also capable of contracting from an open 90 configuration to a closed 90' configuration; this is typical when ECI is withdrawn back into the delivery catheter.

The device 100 of the invention may thus comprise, in a tandem arrangement, the ECI, ECB and IDU, the IDU being disposed at one end of the tandemly arranged elements. Preferably, the IDU is the distal-most element. The IDU in the open configuration delivers the RHV. The IDU in the closed configuration, is configured for passage through the lumen of the delivery catheter. FIGS. 18 to 21 show various configurations of a device 100 of the invention where the IDU 90 is in an open configuration at the distal end of the tandem arrangement. In FIGS. 18 and 19, the IDU 90 is adjacent to the ECB 70, while in FIGS. 20 and 21, the IDU 90 is adjacent to the ECI 50.

Preferably in the closed 90' configuration the IDU has a maximum outer transverse-cross-sectional diameter of 0.2 cm, 0.3 cm, 0.4 cm, 0.5 cm, 0.6 cm, 0.7 cm, 0.8 cm, 0.9 cm or 1 cm, or a value in the range between any two of the aforementioned values, preferably between 0.6 cm to 0.8 cm, preferably about 0.7 cm.

Preferably in the open 90 configuration the IDU has a maximum outer transverse-cross-sectional diameter of 1.6 cm 1.8 cm, 2 cm 2.2 cm 2.4 cm, 2.6 cm, 2.8 cm, 3 cm, 3.2 cm, 3.4 cm, 3.6 cm, or a value in the range between any two of the aforementioned values, preferably between 2.4 cm to 2.8 cm, preferably about 2.6 cm.

The IDU 90, 90' may be radially expandable. The IDU may be non-radially expandable. IDU 90, 90' may comprise an inflatable balloon, over which a balloon-expandable RHV is provided. Inflation of the balloon is used to deploy the RHV. Alternatively, the IDU 90, 90' may comprise a self-expanding RHV which self-expands from the closed configuration to the open configuration.

RHV may take on a number of forms, and are generally known in the art. The implantable RHV exhibit several beneficial characteristics. RHV should preferably be constructed of as little material as possible, and should be easily collapsible. The RHV may be radially compressed or compacted to a size significantly smaller than its deployed diameter for delivery. The implantable valve or support elements of the valve may contain Gothic arch-type structural support elements to efficiently support and maintain the valve once it is implanted.

The RHV 94, 94' may be balloon expandable, that is implanted using a balloon. The RHV 94, 94' may be provided over the balloon. The position of the RVH 94 in relation to the IDU 90, 90' is preferably fixed and known.

Alternatively, the RHV may be self-expanding that can be implanted without the use of a balloon. As such, at least part of the structure may be constructed of NiTinol or some other shape-memory or self-expanding material. The RHV may be deployed by mechanical means, such as by releasing a lasso that surrounds the exterior of RHV or by operating a mechanical expansion device within RHV.

Alternatively, the RHV may be an inflatable RHV that can be implanted without the use of a separate balloon. An inflatable RHV utilizes an inflation medium that expands the RHV to the desired size once in the appropriate position. The inflation medium is one that hardens, thus maintaining the shape of the inflated RHV even after the source of the pressure has been released. An example of an inflatable RHV is the Direct Flow Medical valve manufactured by Direct Flow Medical Inc.

The RHV may have an outer stent that is installed before deploying the valve structure. Valves manufactured in accordance with the principles of the present invention are preferably constructed of biocompatible materials. Some of the materials may be bioabsorbable, so that shortly after the implantation procedure, only the anchoring device and tissue valve remain permanently implanted. The valve leaflets may be composed of homograph valve tissue, animal tissue, valve rebuild material, pericardium, synthetics, or alloys, such as a thin NiTinol mesh.

RHV in accordance with the principles of the present invention may be drug eluding to prevent restenosis by inhibiting cellular division or by preventing reapposition of calcium. The drug may act as an active barrier that prevents the formation of calcium on the valve. Additionally, the drug may stimulate healing of the new valve with the aorta. Furthermore, the implantable valves are preferably treated to resist calcification. The support elements of the implantable valve may be exterior to the valve (e.g., between the new valve tissue and the aorta wall), interior to the valve (e.g., valve tissue is between the support elements and the aorta wall), or may form an endoskeleton of the valve (e.g., support elements of the valve may be within the tissue of the implantable valve).

In some embodiments of the present invention, the new valve may be designed to be exchangeable. Many replacement heart valves have a life expectancy of 10-20 years. Therefore, many patients will require follow-up valve replacements. Certain structural components of the heart valve (e.g., the base ring, hooks, etc.) could be permanent, while the tissue leaflets may be exchangeable. It may be preferable to simply dilate the old valve with the new valve.

According to a preferred aspect the IDU 90, 90' comprises a balloon 92 and RHV 94. The balloon 92 may be elongate. The outer shape of the balloon 92 in the open configuration preferably is at least a partly cylindrical, most preferably having rounded ends. Other outer shapes of the ECB 70 in the open configuration are envisaged for instance, conical, barrel, bullet, rivet and the like. The balloon may be made from any suitable elastomeric polymer material having moisture impermeable properties, able to withstand inflation pressure, such as polyamide (e.g. PA11, PA12), nylons, PEBAX™, polyethylene, latex rubber, elastic, or plastic.

As mentioned earlier, when the device 100 of the invention is used to excise the heart valve via the transapical approach, the support surface 77 of the ECB 70, 70' is pointing in the proximal direction. Accordingly, the IDU 90, 90' may be provided attached to the distal end 30 of the second elongate member 72. Specifically, the IDU 90. 90' may be attached to the second elongate member 72, distal and adjacent to the ECB 70, 70'. IDU 90, 90' is the distal most element of the ECI 50 and ECB 70. Preferably the IDU 90, 90' is held in fixed relation with the ECB 70, 70'. Preferably the distance between the IDU 90, 90' and ECB 70, 70' is fixed. FIGS. 18 and 19 schematically indicate this configuration of elements. FIGS. 22 to 40 also show this arrangement where the second elongate member 72 is within a delivery catheter 40 and disposed in relation to the first elongate member 52. Preferably, a central axis of the second elongate member 72 is co-axial with a central axis of the ECB 70, 70' and with a central axis of the IDU 90, 90'.

Being attached to the second elongate member 72, the IDU 90, 90' may be moved responsive to movements at the proximal end 20. As the IDU 90. 90' is preferably in fixed relation to the ECB 70, 70', both IDU 90, 90' and ECB 70, 70' attached to the second member 72 move in concert. The position of the ECB 70, 70' in relation to the IDU 90, 90' is preferably known.

When the IDU 90, 90' comprises an expansion balloon, as shown, for instance, in FIGS. 22 to 40 the IDU balloon is attached to the distal end of the second elongate member 72, and an IDU balloon lumen is in fluid communication with a SEM second inflation lumen 75 of the second elongate member 72. In FIG. 31 the IDU balloon lumen and SEM second inflation lumen 75 are connected using a port 82. The SEM second inflation lumen 75 may be configured for the passage of inflation fluid (e.g. saline) from a pump in fluid connection with the second inflation lumen 75 at the proximal end of the second elongate member. The SEM second inflation lumen 75 is fluidicly isolated from the SEM first inflation lumen 74 and from the SEM guidewire lumen 76. Preferably, the SEM second inflation lumen 75 is sealed at the distal 30 end, preventing the seepage of inflation fluid from the distal end of the second elongate member.

As mentioned earlier, when the device 100 of the invention is used to excise the heart valve via the transaortic approach, the support surface 77 of the ECB 70, 70' may point in the distal direction 30. Accordingly, the IDU 90, 90' may be provided attached to the distal end 30 of the first elongate member 52. Specifically, the IDU 90. 90' may be attached to the first elongate member 52, distal and adjacent to the ECI 50, 50'. IDU 90, 90' is the distal most element out of the ECI 50 and ECB 70. FIGS. 20 and 21 schematically indicate this configuration of elements. Preferably, a central axis of the first elongate member 52 is co-axial with a central axis of the ECI 50, 50' and with a central axis of the IDU 90, 90'. It will be appreciated that the first elongate member would be provided with the necessary lumens (e.g. inflation lumen) to actuate deployment of the RHV as described elsewhere herein.

Preferably the IDU 90, 90' is held in fixed positional relation with the ECI 50, 50'. Preferably the distance between the IDU 90, 90' and ECI 50, 50' is fixed. Being attached to the first elongate member 52, the IDU 90, 90' may be moved responsive to movements at the proximal end 20. As the IDU 90, 90' is preferably in fixed relation to the ECB 70, 70', both IDU 90, 90' and ECI 50, 50' attached to the first member 52 move in concert. The position of the ECI 50, 50' in relation to the IDU 90, 90' is preferably known.

Preferably, the IDU 90, 90' is configured for rotation around the first elongate member 52. The IDU 90, 90' may be connected to the first elongate member 52 using a revolute joint. By being independently rotatable, torque transmitted from the proximal end 20 of the first elongate member 52 to the ECI 50, 50' is not directly conveyed to the IDU 90, 90', allowing the IDU 90, 90' to remain stationary during rotary cutting.

When the device 100 configured for the transaortic approach, as mentioned previously, the second elongate member 72 may be disposed with a SEM instrument lumen from its proximal end to its distal end, that is open at both ends. The SEM instrument lumen may be configured for the passage of the first elongate member 52 to which the ECI 50, 50' and IDU 90, 90' are operatively attached.

An example of another device 100 of the invention comprising an ECI 50, ECB 70 and IDU 90 is shown in FIGS. 31 and 31A. The device 100 is suitable for excision via the transapical approach. A delivery catheter 40 is indicated, provided with a delivery lumen 42 extending from the proximal to the distal end, that is open at both proximal 20 and distal 30 ends. Disposed in the delivery catheter lumen 42 and in slidable relation thereto is a first elongate member 52 to which a self-expanding ECI 50 is attached to its distal tip. The first elongate member 52 is provided with an FEM instrument lumen 54 extending from the proximal to the distal end, that is open at both proximal 20 and distal 30 ends. The distal open end of the FEM instrument lumen 54 passes into or through the ECI 50 void 64. Disposed in this FEM instrument lumen 54 and in slidable relation thereto is a second elongate member 72 to which an ECB 70 and IDU 90 are distally attached in tandem, the IDU 90 disposed distal to the ECB 70. The ECB 70 comprises an ECB inflatable balloon. The IDU 90 comprises an IDU inflatable balloon 92 over which a RHV 94 is disposed in a known position. The second elongate member 72 is provided with an SEM first inflation lumen 74, extending from the proximal to the distal end, that is open at the proximal 20 end and closed (sealed) at the distal 30 end. The SEM first inflation lumen 74 is in fluid connection with a lumen of the ECB inflatable balloon via a connecting port 80. The second elongate member 72 is also provided with a SEM second inflation lumen 75, extending from the proximal to the distal end, that is open at the proximal 20 end and closed (sealed) at the distal 30 end. The SEM second inflation lumen 75 is in fluid connection with a lumen of the IDU 90 inflatable balloon via a connecting port 82. The second elongate member 72 is further provided with an SEM guidewire lumen 76, extending from the proximal to the distal end, that is open at both proximal 20 and distal 30 ends. The SEM first inflation lumen 74, SEM second inflation lumen 75 and the SEM guidewire lumen 76 are defined by a tubular cavities disposed within the second elongate member 72. The SEM first inflation lumen 74, SEM second inflation lumen 75 and the SEM guidewire lumen 76 are arranged within the delivery catheter lumen 42 in a side-by-side configuration (FIG. 31A). The SEM guidewire lumen 76 has a circular profile, while the SEM first inflation lumen 74 and SEM second inflation lumen 75 have a crescent moon profile. While FIG. 31A depicts circular and crescent moon lumen profiles, it is also conceivable that other profile shapes are adopted, for instance, circular profiles, oval profiles, where the profiles are the same or a mixture of these.

An example of a device 100 of the invention comprising an ECI 50 that comprises an expandable cone, ECB 70 and IDU 90 is shown in FIGS. 29 and 29A. The device 100 is suitable for excision via the transapical approach. A delivery catheter 40 is indicated, provided with a delivery lumen 42 extending from the proximal to the distal end, that is open at both proximal 20 and distal 30 ends. Disposed in the delivery catheter lumen 42 and in slidable relation thereto is a first elongate member 52 to which a self-expanding ECI 50 is attached to its distal tip. The ECI 50 comprises an ECI inflatable balloon 550 positioned within the expandable cone of the ECI 50. The first elongate member (FEM) 52 is provided with an FEM first inflation lumen 554, extending from the proximal to the distal end, that is open at the proximal 20 end and closed (sealed) at the distal 30 end. The FEM first inflation lumen 554 is in fluid connection with a lumen of the ECI inflatable balloon 550 via a connecting port 81. The first elongate member 52 is also provided with an FEM instrument lumen 54 extending from the proximal to the distal end, that is open at both proximal 20 and distal 30 ends. The distal open end of the FEM instrument lumen 54 passes into or through the ECI 50 void 64. The FEM first inflation lumen 554, FEM instrument lumen 54 are arranged concentrically with the FEM first inflation lumen 554, surrounding the FEM instrument lumen 54 (FIG. 29A). Disposed in this FEM instrument lumen 54 and in slidable relation thereto is a second elongate member 72 to which an ECB 70 and IDU 90 are distally attached in tandem, the IDU 90 disposed distal to the ECB 70. The ECB 70 comprises an ECB inflatable balloon. The IDU 90 comprises an IDU inflatable balloon 92 over which a RHV 94 is disposed in a known position. The second elongate member 72 is provided with an SEM first inflation lumen 74, extending from the proximal to the distal end, that is open at the proximal 20 end and closed (sealed) at the distal 30 end. The SEM first inflation lumen 74 is in fluid connection with a lumen of the ECB inflatable balloon via a connecting port 80. The second elongate member 72 is also provided with a SEM second inflation lumen 75, extending from the proximal to the distal end, that is open at the proximal 20 end and closed (sealed) at the distal 30 end. The SEM second inflation lumen 75 is in fluid connection with a lumen of the IDU 90 inflatable balloon via a connecting port 82. The second elongate member 72 is further provided with an SEM guidewire lumen 76, extending from the proximal to the distal end, that is open at both proximal 20 and distal 30 ends. The SEM first inflation lumen 74, SEM second inflation lumen 75 and the SEM guidewire lumen 76 are defined by a tubular cavities disposed within the second elongate member 72. The SEM first inflation lumen 74, SEM second inflation lumen 75 and the SEM guidewire lumen 76 are arranged within the delivery catheter lumen 42 in a side-by-side configuration (FIG. 29A). The SEM guidewire lumen 76 has a circular profile, while the SEM first inflation lumen 74 and SEM second inflation lumen 75 have a crescent profile. While FIG. 29A depicts circular and crescent lumen profiles, it is also conceivable that other profile shapes are adopted, for instance, circular profiles, oval profiles, where the profiles are the same or a mixture of these.

An example of a device 100 of the invention comprising an ECI 50 that comprises an expandable cone, ECB 70 that comprises two balloons one with in the lumen of the other, and IDU 90 is shown in FIGS. 30 and 30A. The device 100 is suitable for excision via the transapical approach. A delivery catheter 40 is indicated, provided with a delivery lumen 42 extending from the proximal to the distal end, that is open at both proximal 20 and distal 30 ends. Disposed in the delivery catheter lumen 42 and in slidable relation thereto is a first elongate member 52 to which a self-expanding ECI 50 is attached to its distal tip. The ECI 50 comprises an ECI inflatable balloon 550 positioned within the expandable cone of the ECI 50. The first elongate member (FEM) 52 is provided with an FEM first inflation lumen 554, extending from the proximal to the distal end, that is open at the proximal 20 end and closed (sealed) at the distal 30 end. The FEM first inflation lumen 554 is in fluid connection with a lumen of the ECI inflatable balloon 550 via a connecting port 81. The first elongate member 52 is also provided with an FEM instrument lumen 54 extending from the proximal to the distal end, that is open at both proximal 20 and distal 30 ends. The distal open end of the FEM instrument lumen 54 passes into or through the ECI 50 void 64. The FEM first inflation lumen 554, FEM instrument lumen 54 are arranged concentrically with the FEM first inflation lumen 554, surrounding the FEM instrument lumen 54 (FIG. 30A). Disposed in this FEM instrument lumen 54 and in slidable relation thereto is a second elongate member 72 to which an ECB 70 and IDU 90 are distally attached in tandem, the IDU 90 disposed distal to the ECB 70. The ECB 70 comprises two ECB inflatable balloons—an outer balloon 71, and an inner balloon 71'; the inner balloon 71' is disposed within a lumen of the outer balloon 71. The second elongate member 72 is provided with an SEM inner-balloon inflation lumen 74, extending from the proximal to the distal end, that is open at the proximal 20 end and closed (sealed) at the distal 30 end. The SEM inner-balloon inflation lumen 74 is in fluid connection with a lumen of the ECB inflatable balloon via a connecting port 80. The second elongate member 72 is also provided with an SEM outer-balloon inflation lumen 73, extending from the proximal to the distal end, that is open at the proximal 20 end and closed (sealed) at the distal 30 end. The SEM outer-balloon inflation lumen 73 is in fluid connection with a lumen of the ECB inflatable balloon via a connecting port 84. The IDU 90 comprises an IDU inflatable balloon 92 over which a RHV 94 is disposed in a known position. The second elongate member 72 is also provided with a SEM IDU inflation lumen 75, extending from the proximal to the distal end, that is open at the proximal 20 end and closed (sealed) at the distal 30 end. The SEM IDU inflation lumen 75 is in fluid connection with a lumen of the IDU 90 inflatable balloon via a connecting port 82. The second elongate member 72 is further provided with an SEM guidewire lumen 76, extending from the proximal to the distal end, that is open at both proximal 20 and distal 30 ends. The SEM inner-balloon inflation lumen 74, the SEM outer-balloon inflation lumen 75, SEM IDU inflation lumen 75 and the SEM guidewire lumen 76 are defined by a tubular cavities disposed within the second elongate member 72. The SEM inner-balloon inflation lumen 74, the SEM outer-balloon inflation lumen 75, SEM IDU inflation lumen 75 and the SEM guidewire lumen 76 are arranged within the delivery catheter lumen 42 in a side-by-side configuration (FIG. 30A). The SEM guidewire lumen 76 has a circular profile, while the SEM inner-balloon inflation lumen 74, the SEM outer-balloon inflation lumen 75, and SEM IDU inflation lumen 75 have a crescent profile. While FIG. 30A depicts circular and crescent lumen profiles, it is also conceivable that other profile shapes are adopted, for instance, circular profiles, oval profiles, where the profiles are the same or a mixture of these.

Figure 35:
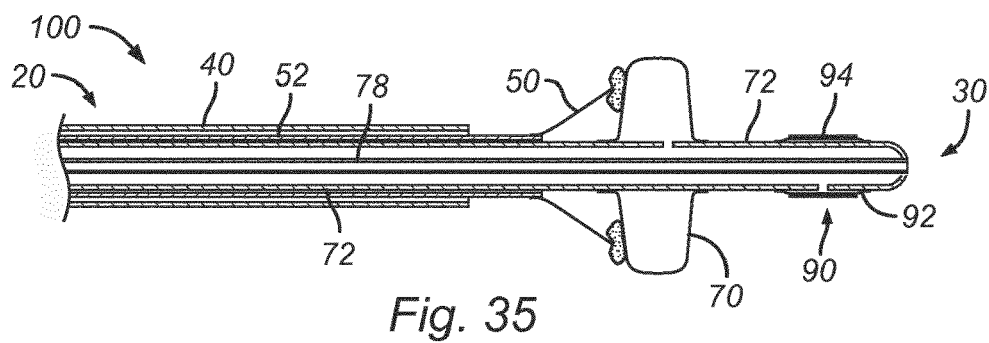
Figure 36:
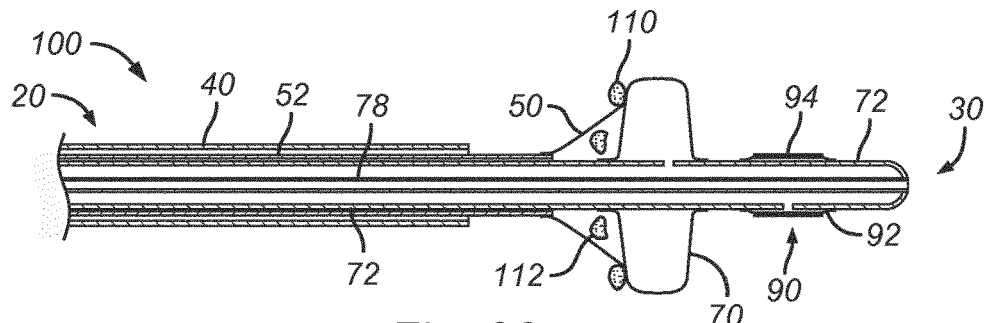

An illustration of a device 100 of the invention comprising an ECI 50, ECB 70 and IDU 90 in use is provided in FIGS. 29 to 40 and described in the following. After delivery of the sheathed device 100 (FIG. 31) to the site of treatment, the ECI 50 is unsheathed (FIG. 32) and expanded by advancement of the first elongate member 52 relative to the delivery catheter 40 from the proximal end 20. The ECI 50 is self-expanding, and formed from a plurality of hinged blades that constitute a truncated cone in the open configuration. The ECB 70—which comprises a balloon—is also advanced distally relative to the delivery catheter 40 responsive to movement of the second elongate member 72 at the proximal end 20. Once the ECB 70 is put into position, it is inflated (FIG. 34); inflation centers the device 100, in particular the ECI 50, and anchors the ECB 70 relative to the vessel wall 110. The ECI 50 in the open configuration, having a cutting edge is advanced distally towards the ECB 70 (FIG. 35).

The heart valve, supported by the ECB 50 is excised using the cutting edge of the ECI 50; excision is assisted by rotation and/or translation of the first elongate member 52 which transmits torque and/or linear force to the cutting edge. The excised valve 112 is captured in the void 64 formed by the open configuration of the ECI 50 (FIG. 36), and is retained by the lid formed by the supporting surface of the ECB 70. The first 52 and second 72 elongate members are retracted into the distal 30 end of the delivery catheter 40 (FIG. 37. Concomitantly, the excised valve 112 is compressed or compacted by radial forces acting on the blades of the ECI 50, applied during withdrawal of the first elongate member 52 into the distal end of the delivery catheter 40 lumen 42. The compression or compaction may be assisted by rotation and/or a longitudinal vibration of the ECI 50 during withdrawal actuated via the proximal end 20 of the first elongate member 52. The excision procedure may be assisted by one or more radio-opaque markers present in the ECI 50 and/or ECB 70. The markers may indicate, for instance, when the ECI 50 and ECB 70 flank the heart valve. Since the IDU 90 is in fixed and known positional relation with the ECB 70, withdrawal of the first elongate member 52 brings the IDU 90 into position for deployment of the RHV 94. Once correctly positioned, the IDU balloon 92 is inflated (FIG. 38) which expands the RHV 94 for deployment. After deployment, the IDU balloon 92 is deflated (FIG. 39). The first 52 and second 72 members are withdrawn through the delivery catheter 40 (FIG. 40).

It will be appreciated that the description above provides only one possible technique for performing a combined excision and replacement using a single device of the present invention. Variations of the technique are possible.

Figure 23:
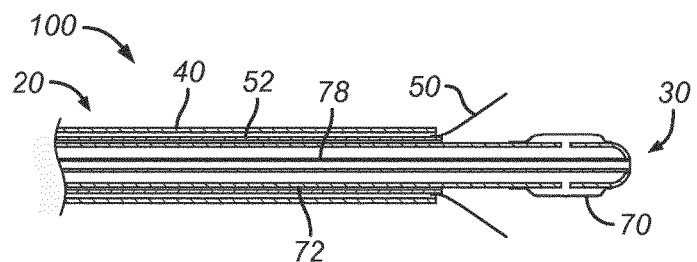
FIGS. 23 to 28 depict steps in the use of a device indicated in FIG. 22 for excising a heart valve.
Figure 24:
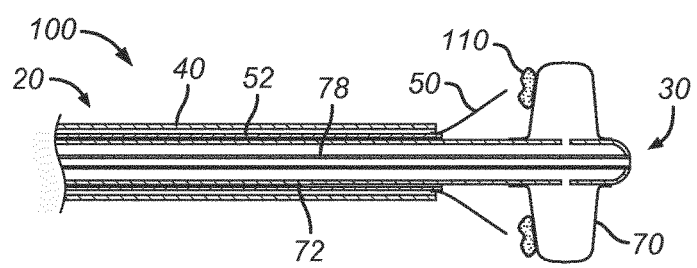

For instance, FIG. 23 shows that the ECI 50 is expanded prior to expansion of the ECB 70; it is equally within the scope of the invention that the ECI 50 is expanded after expansion of the ECB 70, preferably when the ECI 50 is positioned close to the site of excision. By opening the ECI 50 just prior to excision limits the risk of the open blade accidentally damaging the heart tissue.

Figure 37:
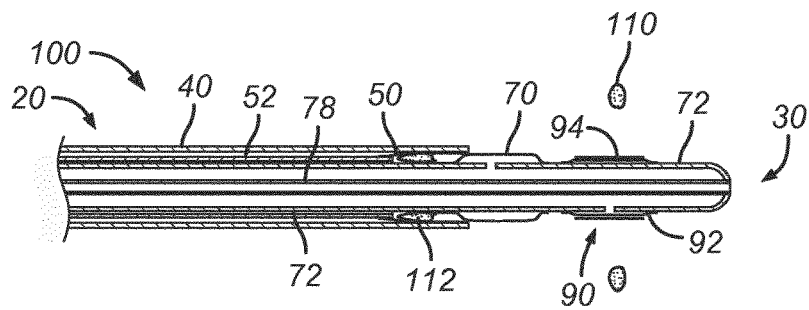
Figure 38:
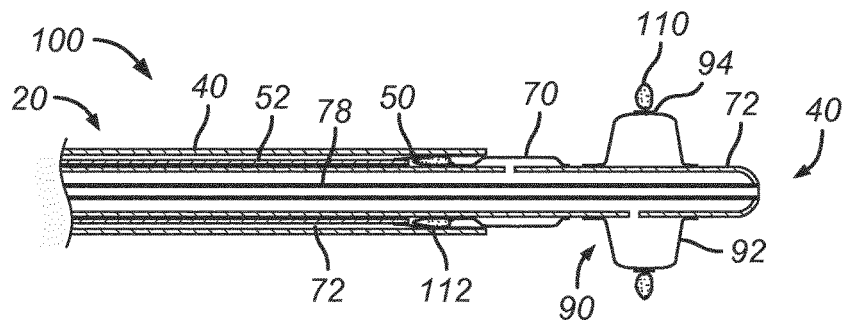
Figure 39:
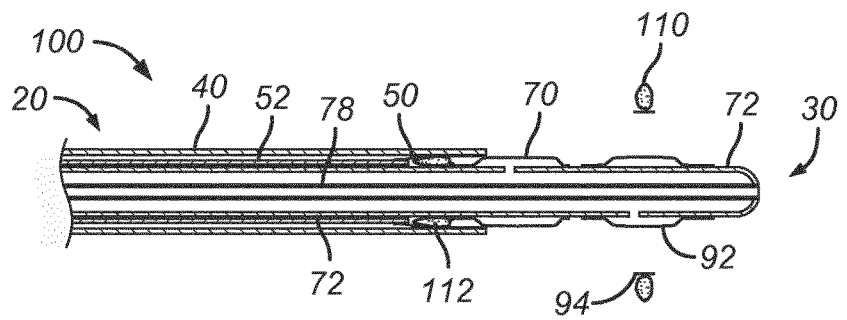
Figure 40:
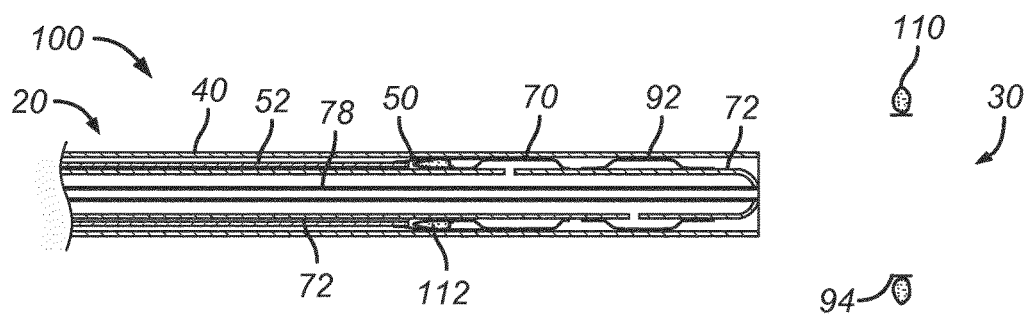

In another variation, FIGS. 38-40 show that the ECI 50 deploys the RHV 92 after compression or compaction of the excised valve in FIG. 37; it is equally within the scope of the invention that the excised valve is compressed or compacted after deployment of the RHV 92. Since compression or compaction of the excised valve can require some time and effort, it can be optimal to perform compression or compaction after the RHV 92 has been placed.

EXAMPLE 1

A stainless-steel conical expandable cone was prepared according to the invention. It was connected to a motor, and used to cut severely stenosed heart valve tissue with calcification buds of 6 mm in diameter. The cutting forces were about 10.5N, the required torque to cut the valve varied between 1.0 and 4 Nm for a resection time comprised between 6 and 17 seconds.

EXAMPLE 2

Figure 41B:
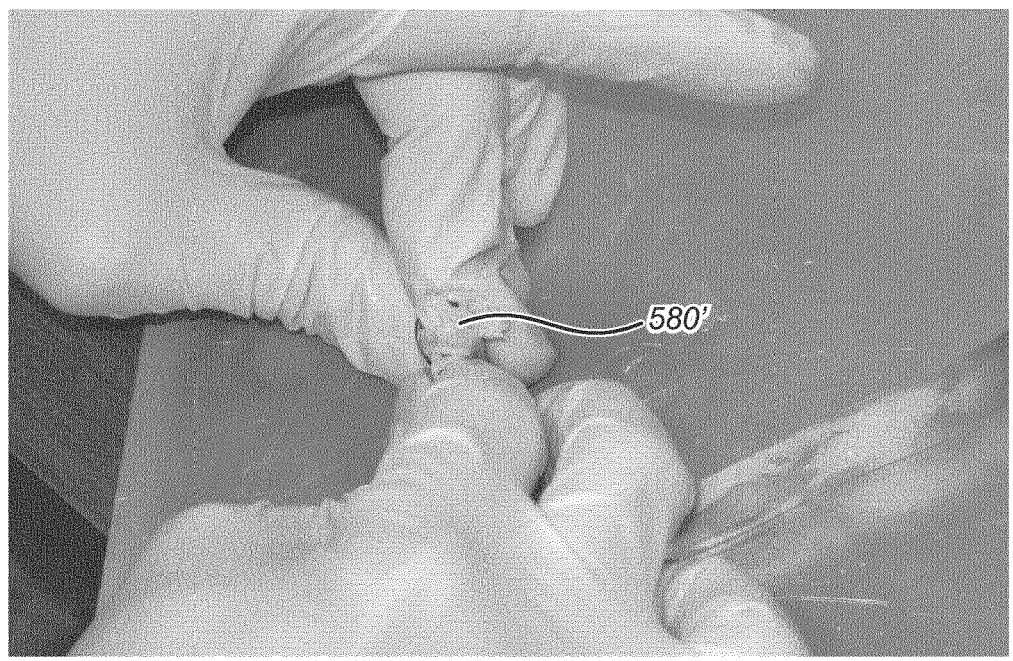

A stainless-steel expandable cone was prepared according to the invention, and was used to compress or compact the excised valve. The valve shown in FIG. 41A and FIG. 41B is the same. As shown in FIG. 41A, the cut valve 580 occupying a large space was compressed or compacted into a cylindrical form 580' shown in FIG. 41B using forces of the wall of the expandable cone applied to the valve. The cylindrical form is suitable for withdrawal through a delivery catheter.

The invention claimed is:

1. A device (100) for the excision of a heart valve via a percutaneous route having a proximal (20) and distal (30) end, comprising:
    a radially expandable cutting instrument, ECI, (50, 50') capable of radial expansion from a closed (50') to an open (50) configuration,
        wherein the open configuration provides a receptacle with a void (64) having an aperture (65) at one end, the distal edge of the aperture (65) forming a cutting edge (66) for excision of the heart valve, which receptacle is configured to receive and contain the excised heart valve,
        wherein the ECI (50') in the closed configuration, is configured for passage through the lumen (42) of a delivery catheter (40), and
        wherein the receptacle is configured to compact and store the excised heart valve by contraction of the ECI from the open (50) to the closed configuration (50');
    an expandable cutting block, ECB, capable of expansion from a closed (70') to an open (70) configuration, disposed adjacent to the cutting edge (66),
        wherein the ECB in the open configuration (70) provides a support surface (77) to support the heart valve under excision by the ECI (50),
        wherein the ECB in the closed configuration (70'), is configured for the passage through the lumen (42) of the delivery catheter (40);
    and
    wherein a distance between the cutting edge (66) and the ECB (70) is adjustable,
    wherein the ECI (50) comprises a sheet of material rolled to form an expandable cone (500) at least partly conical in the open configuration, which sheet of material in an unrolled flat condition comprises a geometric shape of an annulus segment.

2. A device according to claim 1 further comprising a first elongate member (52) and a second elongate member (72), wherein the ECI (50) is attached to a distal end (30) of the first elongate member (52) and the ECB (70) is attached to a distal end (30) of the second elongate member (72), which first and second members are slidable relative to each other thereby adjusting the distance between the cutting edge (66) and the ECB (70).

3. A device according to claim 2, wherein the first elongate member (52) is provided with a lumen (54) extending between the proximal end (20) and the distal end (30) and is open at both ends, configured for the passage of the second elongate member (72).

4. Device according to claim 2, wherein the second elongate member (72) is provided with a guidewire lumen extending between a proximal end (20) and a distal end (30) and is open at both ends, configured for the passage of a guidewire.

5. Device according to claim 2, wherein the ECB (70) comprises an expandable balloon, and the second elongate member (72) is provided with an inflation lumen in fluidic connection with an inflation lumen of said expandable balloon.

6. Device according to claim 2, wherein the ECB (72) comprises two expandable balloons, an outer expandable balloon (71) and an inner expandable balloon (71') provided within a lumen of the outer expandable balloon (71), and the second elongate member (72) is provided with an inner-balloon inflation lumen (74) in fluidic connection with an inflation lumen of said inner-expandable balloon, and with an outer-balloon inflation lumen (73) in fluidic connection with an inflation lumen of said outer-expandable balloon.

7. Device according to claim 2, further comprising an implant deployment unit, (IOU) 90, comprising a replacement heart valve, which IOU (90) is configured to deploy the replacement heart valve upon actuation, wherein the IOU (90) is operatively attached to the second elongate member (72), distal (30) to the ECB (70).

8. Device according to claim 1, further comprising an implant deployment unit, (IOU) 90, comprising a replacement heart valve, which IOU (90) is configured to deploy the replacement heart valve upon actuation.

9. Device according to claim 1, wherein the cutting edge (66) points in a direction towards the distal (30) end and the support surface (77) points in a direction towards the proximal (20) end.

10. Device according to claim 1, wherein the expandable cone is configured to transition from the open to closed configuration by rolling the annulus segment into essentially a cylindrical shape.

11. Device according to claim 10, incorporating the features of claim 2, wherein said rolling actuated by the rotation and proximal displacement of the first elongate member (52) relative to the delivery catheter (40).

12. Device according to claim 1, wherein the ECI (50) and ECB (70) in mutual contact form a closed debris-impermeable receptacle formed by the support surface (77) of the ECB co-operating with the receptacle aperture (66).

13. Device according to claim 8 wherein the IOU (90) comprises an expandable balloon around which the replacement heart valve is disposed, and the replacement heart valve is balloon deployable.

14. Device according to claim 8, wherein the distance between the IDU (90) and the ECB (70) is fixed.

* * * * *